United States Patent
Reddy et al.

(10) Patent No.: US 7,049,110 B2
(45) Date of Patent: May 23, 2006

(54) INACTIVATION OF WEST NILE VIRUS AND MALARIA USING PHOTOSENSITIZERS

(75) Inventors: Heather Reddy, Denver, CO (US); Raymond P. Goodrich, Lakewood, CO (US)

(73) Assignee: Gambro, Inc., Lakewood, CO (US)

( * ) Notice: Subject to any disclaimer, the term of this patent is extended or adjusted under 35 U.S.C. 154(b) by 227 days.

(21) Appl. No.: 10/358,073

(22) Filed: Feb. 3, 2003

(65) Prior Publication Data

US 2004/0018997 A1 Jan. 29, 2004

Related U.S. Application Data

(63) Continuation-in-part of application No. 09/586,147, filed on Jun. 2, 2000, now abandoned, which is a continuation-in-part of application No. 09/357,188, filed on Jul. 20, 1999, now Pat. No. 6,277,337, which is a continuation-in-part of application No. 09/119,666, filed on Jul. 21, 1998, now Pat. No. 6,258,577.

(60) Provisional application No. 60/353,162, filed on Feb. 1, 2002.

(51) Int. Cl.
C12N 13/00 (2006.01)
C12N 7/04 (2006.01)
A61L 2/08 (2006.01)
A61L 2/10 (2006.01)

(52) U.S. Cl. .............................. 435/173.1; 435/173.3; 435/236; 435/446; 422/22; 422/24; 422/28; 422/40; 422/44

(58) Field of Classification Search ............ 435/173.1, 435/173.3, 236, 446; 422/22, 24, 28, 40, 422/44
See application file for complete search history.

(56) References Cited

U.S. PATENT DOCUMENTS

| 683,690 A | 10/1901 | Johnson |
| 1,733,239 A | 10/1929 | Roberts |
| 1,961,700 A | 6/1934 | Moehler ........................ 167/3 |
| 2,056,614 A | 10/1936 | Moehler ........................ 21/18 |
| 2,212,230 A | 8/1940 | Goldmann ................... 250/11 |
| 2,212,330 A | 8/1940 | Thomas ...................... 250/52 |
| 2,340,890 A | 2/1944 | Lang et al. |
| 2,788,014 A | 3/1957 | Tullis |
| 3,456,053 A | 7/1969 | Crawford .................... 424/89 |
| 3,629,071 A | 12/1971 | Sekhar ....................... 195/1.8 |

(Continued)

FOREIGN PATENT DOCUMENTS

EP 0 066 886 6/1982

(Continued)

OTHER PUBLICATIONS

Goodrich, L. et al. Poster. Riboflavin Pathogen Inactivation Process Yields Good Platelet Cell Quality and Expedient Viral Kill. ASH 43rd Annual Meeting. Dec. 2001.

(Continued)

*Primary Examiner*—Robert A. Wax
*Assistant Examiner*—Rosanne Kosson
(74) *Attorney, Agent, or Firm*—Greenlee, Winner and Sullivan, P.C.

(57) ABSTRACT

Methods and apparatuses are provided for inactivation of microorganisms in fluids or on surfaces. Preferably the fluids contain blood or blood products and comprise biologically active proteins. Preferred methods include the steps of adding an effective, non-toxic amount of a photosensitizer to a fluid and exposing the fluid to photoradiation sufficient to activate the photosensitizer whereby microorganisms are inactivated.

18 Claims, 6 Drawing Sheets

U.S. PATENT DOCUMENTS

| | | | |
|---|---|---|---|
| 3,683,177 A | 8/1972 | Veloz | 250/43 |
| 3,683,183 A | 8/1972 | Vizzini et al. | 250/44 |
| 3,705,985 A | 12/1972 | Manning et al. | 250/106 S |
| 3,776,694 A | 12/1973 | Leittl | 21/102 R |
| 3,852,032 A | 12/1974 | Urbach | 21/54 |
| 3,864,081 A | 2/1975 | Logrippo | 21/102 R |
| 3,874,384 A | 4/1975 | Deindoerfer et al. | 128/272 |
| 3,894,236 A | 7/1975 | Hazelrigg | 250/435 |
| 3,926,556 A | 12/1975 | Boucher | 21/54 R |
| 3,927,325 A | 12/1975 | Hungate et al. | 250/435 |
| 4,061,537 A | 12/1977 | Seiler et al. | |
| 4,112,070 A | 9/1978 | Harmening | |
| 4,124,598 A | 11/1978 | Hearst et al. | 260/343.21 |
| 4,139,348 A | 2/1979 | Swartz | 23/232 E |
| 4,169,204 A | 9/1979 | Hearst et al. | 546/270 |
| 4,173,631 A | 11/1979 | Graham et al. | |
| 4,181,128 A | 1/1980 | Swartz | 128/207.21 |
| 4,196,281 A | 4/1980 | Hearst et al. | 536/28 |
| 4,264,601 A | 4/1981 | Trachewsky | |
| 4,267,269 A | 5/1981 | Grode et al. | 435/2 |
| 4,312,883 A | 1/1982 | Baccichetti et al. | 424/279 |
| 4,321,918 A | 3/1982 | Clark, II | 128/124 R |
| 4,321,919 A | 3/1982 | Edelson | 128/124 R |
| 4,336,809 A | 6/1982 | Clark | 128/665 |
| 4,390,619 A | 6/1983 | Harmening-Pittiglio | 435/2 |
| 4,398,031 A | 8/1983 | Bender et al. | 549/282 |
| 4,398,906 A | 8/1983 | Edelson | 604/6 |
| 4,402,318 A | 9/1983 | Edelson | 604/6 |
| 4,407,282 A | 10/1983 | Swartz | 604/20 |
| 4,421,987 A | 12/1983 | Herold | 250/492.1 |
| 4,424,201 A | 1/1984 | Valinsky et al. | 424/3 |
| 4,428,744 A | 1/1984 | Edelson | 604/6 |
| 4,432,750 A | 2/1984 | Estep | 604/4 |
| 4,456,512 A | 6/1984 | Bieler et al. | 204/162 R |
| 4,457,918 A | 7/1984 | Holick et al. | |
| 4,464,166 A | 8/1984 | Edelson | 604/6 |
| 4,467,206 A | 8/1984 | Taylor et al. | 250/435 |
| 4,481,167 A | 11/1984 | Ginter et al. | 422/29 |
| 4,493,981 A | 1/1985 | Payne | 219/450 |
| 4,568,328 A | 2/1986 | King | 604/6 |
| 4,572,899 A | 2/1986 | Walker et al. | 436/18 |
| 4,573,960 A | 3/1986 | Goss | 604/6 |
| 4,573,961 A | 3/1986 | King | 604/6 |
| 4,573,962 A | 3/1986 | Troutner | 604/6 |
| 4,576,143 A | 3/1986 | Clark, III | 128/1 R |
| 4,578,056 A | 3/1986 | King et al. | 604/6 |
| 4,585,735 A | 4/1986 | Meryman et al. | 435/2 |
| 4,596,547 A | 6/1986 | Troutner | 604/4 |
| 4,604,356 A | 8/1986 | Blake, II | 435/194 |
| 4,608,255 A | 8/1986 | Kahn et al. | 424/101 |
| 4,609,372 A | 9/1986 | Carmen et al. | 604/262 |
| 4,612,007 A | 9/1986 | Edelson | 604/5 |
| 4,613,322 A | 9/1986 | Edelson | 604/6 |
| 4,614,190 A | 9/1986 | Stanco et al. | 128/395 |
| 4,623,328 A | 11/1986 | Hartranft | 604/4 |
| 4,626,431 A | 12/1986 | Batchelor et al. | 424/101 |
| 4,642,171 A | 2/1987 | Sekine et al. | 204/298 |
| 4,645,649 A | 2/1987 | Nagao | 422/186.3 |
| 4,648,992 A | 3/1987 | Graf et al. | 540/124 |
| 4,649,151 A | 3/1987 | Dougherty et al. | 514/410 |
| 4,651,739 A | 3/1987 | Oseroff et al. | 128/395 |
| 4,675,185 A | 6/1987 | Kandler et al. | 424/101 |
| 4,683,195 A | 7/1987 | Mullis et al. | 435/6 |
| 4,683,202 A | 7/1987 | Mullis | 435/91 |
| 4,683,889 A | 8/1987 | Edelson | 128/395 |
| 4,684,521 A | 8/1987 | Edelson | 424/101 |
| 4,693,981 A | 9/1987 | Wiesehahn et al. | 435/238 |
| 4,695,460 A | 9/1987 | Holme | 424/101 |
| 4,704,352 A | 11/1987 | Miripol et al. | 435/2 |
| 4,708,715 A | 11/1987 | Troutner et al. | 604/6 |
| 4,726,949 A | 2/1988 | Miripol et al. | 424/101 |
| 4,727,027 A | 2/1988 | Wiesehahn et al. | 435/173 |
| 4,737,140 A | 4/1988 | Lee et al. | 604/4 |
| 4,748,120 A | 5/1988 | Wiesehahn | 435/173 |
| 4,769,318 A | 9/1988 | Hamasaki et al. | 435/2 |
| 4,775,625 A | 10/1988 | Sieber | 435/238 |
| 4,788,038 A | 11/1988 | Matsunaga | 422/22 |
| RE32,874 E | 2/1989 | Rock et al. | 424/101 |
| 4,828,976 A | 5/1989 | Murphy | 435/2 |
| 4,831,268 A | 5/1989 | Fisch et al. | 250/432 R |
| 4,833,165 A | 5/1989 | Louderback | 514/694 |
| 4,861,704 A | 8/1989 | Reemtsma et al. | 435/1 |
| 4,866,282 A | 9/1989 | Miripol et al. | 250/455.1 |
| 4,878,891 A | 11/1989 | Judy et al. | 604/5 |
| 4,880,788 A | 11/1989 | Moake et al. | 514/150 |
| 4,915,683 A | 4/1990 | Sieber | 128/665 |
| 4,921,473 A | 5/1990 | Lee et al. | 494/27 |
| 4,925,665 A | 5/1990 | Murphy | 424/532 |
| 4,930,516 A | 6/1990 | Alfano et al. | 128/665 |
| 4,946,438 A | 8/1990 | Reemtsma et al. | 604/53 |
| 4,948,980 A | 8/1990 | Wedekamp | 250/504 R |
| 4,950,665 A | 8/1990 | Floyd | 514/222.8 |
| 4,952,812 A | 8/1990 | Miripol et al. | 250/455.1 |
| 4,960,408 A | 10/1990 | Klainer et al. | 604/4 |
| 4,961,928 A | 10/1990 | Holme et al. | 424/533 |
| 4,978,688 A | 12/1990 | Louderback | 514/722 |
| 4,986,628 A | 1/1991 | Lozhenko et al. | 350/96.29 |
| 4,992,363 A | 2/1991 | Murphy | 435/2 |
| 4,994,367 A | 2/1991 | Bode et al. | 435/2 |
| 4,998,931 A | 3/1991 | Slichter et al. | 604/20 |
| 4,999,375 A | 3/1991 | Bachynsky et al. | 514/455 |
| 5,011,695 A | 4/1991 | Dichtelmuller et al. | 424/529 |
| 5,017,338 A | 5/1991 | Surgenor | 422/41 |
| 5,020,995 A | 6/1991 | Levy | 433/215 |
| 5,030,200 A | 7/1991 | Judy et al. | 604/5 |
| 5,039,483 A | 8/1991 | Sieber et al. | 422/28 |
| 5,041,078 A | 8/1991 | Matthews et al. | 604/4 |
| 5,089,146 A | 2/1992 | Carmen et al. | 210/782 |
| 5,089,384 A | 2/1992 | Hale | 435/2 |
| 5,092,773 A | 3/1992 | Levy | 433/224 |
| 5,114,670 A | 5/1992 | Duffey | 422/24 |
| 5,114,957 A | 5/1992 | Hendler et al. | 514/356 |
| 5,120,649 A | 6/1992 | Horowitz et al. | 435/713 |
| 5,123,902 A | 6/1992 | Müller et al. | 604/21 |
| 5,133,932 A | 7/1992 | Gunn et al. | 422/24 |
| 5,147,776 A | 9/1992 | Koerner, Jr. | 435/2 |
| 5,149,718 A | 9/1992 | Meruelo et al. | 514/732 |
| 5,150,705 A | 9/1992 | Stinson | 128/396 |
| 5,166,528 A | 11/1992 | Le Vay | 250/455.11 |
| 5,184,020 A | 2/1993 | Hearst et al. | 250/455.11 |
| 5,185,532 A | 2/1993 | Zabsky et al. | 250/455.11 |
| 5,192,264 A | 3/1993 | Fossel | 604/4 |
| 5,211,960 A | 5/1993 | Babior | |
| 5,216,251 A | 6/1993 | Matschke | 250/455.11 |
| 5,229,081 A | 7/1993 | Suda | 427/186 |
| 5,232,844 A | 8/1993 | Horowitz et al. | 435/173.1 |
| 5,234,808 A | 8/1993 | Murphy | 435/2 |
| 5,236,716 A | 8/1993 | Carmen et al. | 424/532 |
| 5,247,178 A | 9/1993 | Ury et al. | 250/438 |
| 5,248,506 A | 9/1993 | Holme et al. | 424/533 |
| 5,250,303 A | 10/1993 | Meryman et al. | 424/533 |
| 5,258,124 A | 11/1993 | Bolton et al. | 210/748 |
| 5,269,946 A | 12/1993 | Goldhaber et al. | 210/767 |
| 5,273,713 A | 12/1993 | Levy | 422/22 |
| 5,281,392 A | 1/1994 | Rubinstein | |
| 5,288,605 A | 2/1994 | Lin et al. | 435/902 |
| 5,288,647 A | 2/1994 | Zimlich, Jr. et al. | 436/174 |
| 5,290,221 A | 3/1994 | Wolf, Jr. et al. | 604/4 |
| 5,300,019 A | 4/1994 | Bischof et al. | 604/4 |
| 5,304,113 A | 4/1994 | Sieber et al. | 604/4 |
| 5,318,023 A | 6/1994 | Vari et al. | 128/633 |
| 5,340,716 A | 8/1994 | Ullman et al. | 435/6 |
| 5,342,752 A | 8/1994 | Platz et al. | 435/2 |
| 5,344,752 A | 9/1994 | Murphy | 435/2 |

| | | | |
|---|---|---|---|
| 5,344,918 A | 9/1994 | Dazey et al. .................. 530/381 |
| 5,358,844 A | 10/1994 | Stossel et al. .................... 435/2 |
| 5,360,734 A | 11/1994 | Chapman et al. ............. 435/238 |
| 5,366,440 A | 11/1994 | Fossel ............................... 604/4 |
| 5,376,524 A | 12/1994 | Murphy et al. ................... 435/2 |
| 5,378,601 A | 1/1995 | Gepner-Puszkin .............. 435/2 |
| 5,418,130 A | 5/1995 | Platz et al. ....................... 435/2 |
| 5,419,759 A | 5/1995 | Naficy ............................. 604/5 |
| 5,427,695 A | 6/1995 | Brown ......................... 210/805 |
| 5,433,738 A | 7/1995 | Stinson ........................ 607/92 |
| 5,459,030 A | 10/1995 | Lin et al. ......................... 435/2 |
| 5,466,573 A | 11/1995 | Murphy et al. ................... 435/2 |
| 5,474,891 A | 12/1995 | Murphy ......................... 435/2 |
| 5,482,828 A | 1/1996 | Lin et al. ......................... 435/2 |
| 5,487,971 A | 1/1996 | Holme et al. .................... 435/2 |
| 5,494,590 A | 2/1996 | Smith et al. ................. 210/782 |
| 5,503,721 A | 4/1996 | Hearst et al. ............. 204/157.6 |
| 5,512,187 A | 4/1996 | Buchholz et al. |
| 5,516,629 A | 5/1996 | Park et al. ....................... 435/2 |
| 5,527,704 A | 6/1996 | Wolf, Jr. et al. ......... 435/283.1 |
| 5,536,238 A | 7/1996 | Bischof ........................... 604/6 |
| 5,545,516 A | 8/1996 | Wagner ........................... 435/2 |
| 5,547,635 A | 8/1996 | Duthie, Jr. ....................... 422/24 |
| 5,550,111 A | 8/1996 | Suhadolnik et al. ............ 514/44 |
| 5,556,958 A | 9/1996 | Carroll et al. ................ 536/25.3 |
| 5,556,993 A | 9/1996 | Wollowitz et al. ........... 549/282 |
| 5,557,098 A | 9/1996 | D'Silva .................... 250/222.1 |
| 5,569,579 A | 10/1996 | Murphy ......................... 435/2 |
| 5,571,666 A | 11/1996 | Floyd et al. .................... 435/2 |
| 5,587,490 A | 12/1996 | Goodrich, Jr. et al. ...... 549/282 |
| 5,593,823 A | 1/1997 | Wollowitz et al. ............. 435/2 |
| 5,597,722 A | 1/1997 | Chapman et al. ............ 435/238 |
| 5,607,924 A | 3/1997 | Magda et al. ............... 514/44 |
| 5,622,867 A | 4/1997 | Livesey et al. ................. 436/18 |
| 5,624,435 A | 4/1997 | Furumoto et al. ............. 606/10 |
| 5,624,794 A | 4/1997 | Bitensky et al. ................ 435/2 |
| 5,628,727 A | 5/1997 | Hakky et al. .................. 604/6 |
| 5,639,376 A | 6/1997 | Lee et al. .................... 210/645 |
| 5,639,382 A | 6/1997 | Brown ...................... 210/739 |
| 5,643,334 A | 7/1997 | Eckhouse et al. ............. 607/88 |
| 5,652,096 A | 7/1997 | Cimino ........................... 435/6 |
| 5,653,887 A | 8/1997 | Wahl et al. ................. 210/745 |
| 5,654,443 A | 8/1997 | Wollowitz et al. .......... 549/282 |
| 5,656,154 A | 8/1997 | Meryman |
| 5,656,498 A | 8/1997 | Iijima et al. |
| 5,658,530 A | 8/1997 | Dunn .......................... 422/24 |
| 5,658,722 A | 8/1997 | Margolis-Nunno et al. .... 435/2 |
| 5,683,661 A | 11/1997 | Hearst et al. ............. 422/186.3 |
| 5,683,768 A | 11/1997 | Shang et al. ................ 428/35.2 |
| 5,686,436 A | 11/1997 | Van Dyke .................. 514/171 |
| 5,688,475 A | 11/1997 | Duthie, Jr. ................. 422/186.3 |
| 5,691,132 A | 11/1997 | Wollowitz et al. ............. 435/2 |
| 5,698,524 A | 12/1997 | Mach et al. .................. 514/22 |
| 5,698,677 A | 12/1997 | Eibl et al. ................... 530/381 |
| 5,702,684 A | 12/1997 | McCoy et al. .............. 424/10.3 |
| 5,707,401 A | 1/1998 | Talmore ...................... 607/88 |
| 5,709,653 A | 1/1998 | Leone ........................ 604/20 |
| 5,709,991 A | 1/1998 | Lin et al. ....................... 435/2 |
| 5,709,992 A | 1/1998 | Rubinstein |
| 5,712,085 A | 1/1998 | Wollowitz et al. ........... 465/148 |
| 5,712,086 A | 1/1998 | Horowitz et al. ............... 435/2 |
| 5,714,328 A | 2/1998 | Magda et al. ................... 435/6 |
| 5,736,313 A | 4/1998 | Spargo et al. .................. 435/2 |
| 5,739,013 A | 4/1998 | Budowsky et al. ........ 435/91.1 |
| 5,753,428 A | 5/1998 | Yuasa et al. .................... 435/2 |
| 5,756,553 A | 5/1998 | Iguchi et al. .............. 514/772.3 |
| 5,769,839 A | 6/1998 | Carmen et al. ............. 604/408 |
| 5,772,960 A | 6/1998 | Ito et al. ....................... 422/41 |
| 5,783,093 A | 7/1998 | Holme ...................... 210/767 |
| 5,789,150 A | 8/1998 | Margolis-Nunno et al. .... 435/2 |
| 5,789,151 A | 8/1998 | Bitensky et al. ............... 435/2 |
| 5,789,601 A | 8/1998 | Park et al. ................... 549/283 |
| 5,798,238 A | 8/1998 | Goodrich, Jr. et al. ... 435/173.3 |
| 5,798,523 A | 8/1998 | Villenueve et al. ......... 250/234 |
| 5,817,519 A | 10/1998 | Zelmanovic et al. ......... 436/63 |
| 5,827,644 A | 10/1998 | Floyd et al. .................... 435/2 |
| 5,834,198 A | 11/1998 | Famulok et al. ................ 435/6 |
| 5,840,252 A | 11/1998 | Giertych ...................... 422/40 |
| 5,843,459 A | 12/1998 | Wang et al. ............. 424/231.1 |
| 5,846,961 A | 12/1998 | Van Dyke .................. 514/171 |
| 5,854,967 A | 12/1998 | Hearst et al. ............ 422/186.3 |
| 5,866,074 A | 2/1999 | Chapman et al. ........ 422/82.09 |
| 5,868,695 A | 2/1999 | Wolf, Jr. et al. ................ 604/4 |
| 5,869,701 A | 2/1999 | Park et al. ................... 549/283 |
| 5,871,900 A | 2/1999 | Wollowitz et al. ............. 435/2 |
| 5,876,676 A | 3/1999 | Stossel et al. ................ 422/12 |
| 5,899,874 A | 5/1999 | Jonsson ........................ 604/4 |
| 5,906,915 A | 5/1999 | Payrat et al. .................... 435/2 |
| 5,908,742 A | 6/1999 | Lin et al. ........................ 435/2 |
| 5,919,614 A | 7/1999 | Livesey et al. |
| 5,922,278 A | 7/1999 | Chapman et al. ............. 422/22 |
| 5,935,092 A | 8/1999 | Sun et al. ....................... 604/4 |
| 5,955,256 A | 9/1999 | Sowemimo-Coker et al. . 435/2 |
| 5,955,257 A | 9/1999 | Burger et al. ................... 435/2 |
| 5,965,349 A | 10/1999 | Lin et al. ........................ 435/2 |
| 5,976,884 A | 11/1999 | Chapman et al. ............. 436/34 |
| 5,985,331 A | 11/1999 | Gottlieb et al. .............. 424/529 |
| 6,017,691 A | 1/2000 | Wollowitz et al. ............. 435/2 |
| 6,020,333 A | 2/2000 | Berque ....................... 514/251 |
| 6,060,233 A | 5/2000 | Wiggins |
| 6,063,624 A | 5/2000 | Kandler et al. |
| 6,200,287 B1 | 3/2001 | Keller et al. ................. 604/260 |
| 6,258,577 B1* | 7/2001 | Goodrich et al. ........ 435/173.3 |
| 6,268,120 B1 | 7/2001 | Platz et al. ..................... 435/2 |
| 6,277,337 B1 | 8/2001 | Goodrich, Jr. et al. ... 422/186.3 |
| 6,843,961 B1* | 1/2005 | Hlavinka et al. ............. 422/24 |

FOREIGN PATENT DOCUMENTS

| | | |
|---|---|---|
| EP | 0 066886 | 6/1982 |
| EP | 0 124 363 | 4/1984 |
| EP | 0108588 | 5/1984 |
| EP | 0 196 515 A1 | 3/1986 |
| EP | 0 184 331 A2 | 6/1986 |
| EP | 0 491/757 | 9/1990 |
| EP | 0 491 757 B1 | 9/1990 |
| EP | 0 525 138 B1 | 12/1991 |
| EP | 0590514 A1 | 4/1994 |
| EP | 0 679 398 A | 11/1995 |
| EP | 0 679 398 A1 | 11/1995 |
| EP | 0 510 185 B1 | 12/1996 |
| EP | 0510185 B1 | 12/1996 |
| EP | 0754461 A2 | 1/1997 |
| EP | 0 801 072 A2 | 3/1997 |
| EP | 0 801 072 A2 | 10/1997 |
| FR | 2674753 | 10/1992 |
| FR | 2715303 | 7/1995 |
| FR | 2718353 | 10/1995 |
| GB | 2034463 A | 6/1980 |
| JP | 59020218 A | 2/1984 |
| WO | WO 83/02328 | 7/1983 |
| WO | WO 85/02116 | 5/1985 |
| WO | WO 88/10087 | 12/1988 |
| WO | WO 89/06702 | 7/1989 |
| WO | WO 90/00059 | 1/1990 |
| WO | WO 91/02529 | 3/1991 |
| WO | WO 92/08348 | 5/1992 |
| WO | WO 92/08349 | 5/1992 |
| WO | WO 92/11057 | 7/1992 |
| WO | WO 92/17173 | 10/1992 |
| WO | WO 93/00005 | 1/1993 |
| WO | WO 94/07426 | 4/1994 |
| WO | WO 94/07499 | 4/1994 |
| WO | WO 94/28120 | 8/1994 |
| WO | WO 95/02325 | 1/1995 |
| WO | WO 95/11028 | 4/1995 |

| | | |
|---|---|---|
| WO | WO 95/12973 | 5/1995 |
| WO | WO 95/16348 | 6/1995 |
| WO | WO 96/14740 | 5/1996 |
| WO | WO 96/14741 | 5/1996 |
| WO | WO 96/39816 | 12/1996 |
| WO | WO 97/07674 | 3/1997 |
| WO | WO 97/18844 | 5/1997 |
| WO | WO 97/22245 | 6/1997 |
| WO | WO 97/36581 | 10/1997 |
| WO | WO 97/36634 | 10/1997 |
| WO | WO 96/06647 | 11/1997 |
| WO | WO 97/46271 | 12/1997 |
| WO | WO 98/30545 | 7/1998 |
| WO | WO 98/31219 | 7/1998 |
| WO | WO 98/41087 | 9/1998 |
| WO | WO 98/51147 | 11/1998 |
| WO | WO 98/56247 | 12/1998 |
| WO | WO 99/11305 | 3/1999 |
| WO | WO 99/59645 | 11/1999 |
| WO | WO 00/04930 | 3/2000 |
| WO | WO 00/11946 | 3/2000 |
| WO | WO 00/20045 | 4/2000 |
| WO | WO 01/28599 | 4/2001 |
| WO | WO 01/78792 | 10/2001 |
| WO | WO 01/96340 | 12/2001 |

OTHER PUBLICATIONS

McAteer, MJ, et al. Poster. Photoinactivation of virus in packed red blood cells using riboflavin and visible light. AABB 53$^{rd}$ Annual Meeting. Nov. 2000.

Samar, R., et al. Poster. Viral Inactivation in Plasma Using Riboflavin-Based Technology. AABB 54$^{th}$ Annual Meeting. Oct. 2001.

Goodrich R.P. The use of riboflavin for the inactivation of pathogens in blood products. *Vox Sang.* 2000;78(suppl 2):211-15.

Cadet, J. et al., "Mechanisms and Products of Photosensitized Degradation of Nucleic Acids and Related Model Compounds," (1983) *Israel J. Chem.* 23:420-429.

Chow, C.S. and Barton, J.K., "Recognition of G-U mismatches by tris(4,7-diphenyl-1,10-phenanthroline)rhodium(III)," (1992) *Biochemistry* 31(24):5423-5429.

Ennever, J.F. and Speck, W.T., "Short Communication. Photochemical Reactions of Riboflavin: Covalent Binding to DNA and to Poly (dA)·Poly (dT)," (1983) *Pediatr. Res.* 17:234-236.

Goodrich, R.P. and Platz, M.S., "The design and development of selective, photoactivated drugs for sterilization of blood products," (1997) *Drugs of the Future* 22(2):159-171.

Joshi, P.C., "Comparison of the DNA-damaging property of photosensitized riboflavin via singlet oxygen ($^1O_2$) and superoxide radical ($O_i$) mechanisms," (1985) *Toxicology Letters* 26:211-217.

Kabuta, H. et al. (1978), "Inactivation of viruses by dyes and visible light," Chem. Abstracts 87(1), Abstract No. 400626.

Kale, H. et al. (1992), "Assessment of the genotoxic potential of riboflavin and lumiflavin; B. Effect of light," Mutation Res. 298:17-23.

Korycka-Dahl, M. and Richardson, T., "Photodegradation of DNA with fluorescent light in the presence of riboflavin, and photoprotection by flavin triplet-state quenchers," (1980) *Biochimica et Biophysica Acta* 610:229-234.

Kovalsky, O.I. and Budowsky, E.I., "Laser (Two-Quantum) Photolysis of Polynucleotides and Nucleoproteins: Quantitative Processing of Results," 1990, *Photochemistry and Photobiology* 5(6):659-665.

Kuratomi, K. and Kobayashi, Y., "Studies on the Interactions Between DNA and Flavins," (1977) *Biochemica et Biophysica Acta* 476:207-217.

Maddox, J., "The working of vitamin K," (1991) *Nature* 353(6346):695.

Matthews, J.L. et al., "Photodynamic therapy of viral contaminants with potential for blood banking applications," (1988) *Transfusion* 28(1):81-83.

Murata, A. et al., "Effect of vitamins other than vitamin C on viruses: virus-inactivating activity of vitamin K5," (1983) *J. Nutr. Sci. Vitaminol (Tokyo)* 29(6):721-724.

Naseem, I. et al., "Effect of alkylated and intercalated DNA on the generation of superoxide anion by riboflavin," (1988) *Bioscience Reports* 8(5):485-492.

North, J. et al. (1993), "New Trends in Photobiology (Invited Review)," J. Photochem. Photobiol. B: Biol. 17:99-108.

Peak, J.G. et al., "DNA Breakage Caused by 334-nm Ultraviolet Light is Enhanced by Naturally Occurring Nucleic Acid Components and Nucleotide Coenzymes," (1984) *Photochemistry and Photobiology* 39(5):713-716.

Piette, J. et al., "Alteration of Guanine Residues During Proflaving Mediated Photosensitization of DNA," (1981) *Photochemistry and Photobiology* 33:325-333.

Piette, J. et al., "Production of Breaks in Single- and Double-Stranded Forms of Bacteriophage φX174 DNA by Proflavine and Light Treatment," (1979) *Photochemistry and Photobiology* 30:369-378.

Pratt, R. et al., "Vitamin K$_5$ as an Antimicrobial Medicament and Preservative," (1950) *J. Am. Pharm. Ass'n* 39(3):127-134.

Speck, W.T. et al., "Further Observations on the Photooxidation of DNA in the Presence of Riboflavin," (1976) *Biochimica et Biphysica Acta* 435:39-44.

Tsugita, A. et al., "Photosensitized inactivation of ribonucleic acids in the presence of riboflavin," (1965) *Biochim. Biophys. Acta* 103:360-363.

Uehara K et al, "Effect of adenine on the riboflavin-sensitized photoreaction. II. Effect of adenine on the photodynamic inactivation of transforming deoxyribonucleic acid in the presence of riboflavin", The Journal of Biochemistry, vol. 71, No. 5, 1972, pp. 805-810.

Uehara K et al, "Effect of adenine on the riboflavin-sensitized photoreaction. I. Effect of adenine on the photodynamic inactivation of yeast alcohol dehydrogenase in the presence of riboflavin," The Journal of Vitaminology, vol. 17, No. 3, 1971, pp. 148-154.

Reinhardt A et al, "Virucidal activity of retinal," Antimicrobial Agents and Chemotherapy, vol. 16, No. 3, Sep. 1979, pp. 421-423.

Cobe Laboratories, Inc, International Search Report for PCT/US99/16404, Filing Date Jul. 21, 1999.

Angreu, G., Boccaccio, C., Lecrubier, C. and Fretault, J. *"UV-B Irradiation of Platelet Concentrates (PC): Feasibility in Transfusion Practice,"* Blood Bank Hematology and Biophysics Laboratories, Abstract Supplement, Abstract S146, Abstract No.: 42S.

Cadet, J., Dacarroz, C. Wang, S.Y. and Midden, W.R., *"Mechanisms and Products of Photosensitized Degradation of Nucleic Acids and Related Model Compounds,"* Israel Journal of Chemistry, vol. 23 (1983) pp. 420-429.

Cole, M., Stromberg, L. Friedman, L. Benade, L. and Shumaker, J., *"Photochemical Inactivation of Virus in Red Cells,"* American Red Cross, Abstract Supplement, Abstract S145, Abstract No.: 42S.

Ennever, John F. and Speck, William T., "Short Communication. Photochemical Reactions of Riboflavin: covalent Binding to DNA and to Poly (dA) Poly (dT)," Pediatr. Res. 17: (1983) pp. 234-236.

Hoffmann, Edwiges M. and Meneghini, Rogerio, "DNA Strand Breaks in mammalian Cells Exposed to Light in the Presence of Riboflavin and Tryptophan," Photochemistry and Photobiology vol. 29, pp. 299-303 (1979).

Korycka-Dahl, Maigorzata and Richardson, Thomas, "Photodegradation of DNA with Fluorescent Light in the Presence of Riboflavin and Photoprotection by Flavin Triplet-State Quenchers," Biochimica et Biophysica Acta, 610 (1980) pp. 229-234.

Kuratomi, Kazuoki and Kobayashi, Yasuko "Studies on the interactions Between DNA and Flavins," Biochimica et Biophysica Acta, 476 (1977) pp. 207-217.

Neyndorff, H.C., Bartel, F., Tufaro, and Levy, J.G., "Development Of A Model To Demonstrate Photosensitizer-mediated Viral Inactivation in Blood," Quadra Logic Technologies, Inc., and the Department of Microbiology, University of British Columbia 485-490 (Feb. 6, 1990).

Peak, J.G., Peak, M.J. and MacCoss, M., "DNA Breakage caused by 334-nm Ultraviolet Light is Enhanced by Naturally Occurring Nucleic Acid Components and Nucleotide Coenzymes," Photochemistry and Photobiology vol. 39, (1984) pp. 713-716.

Piette, J. Calberg-Bacq, C.M., and Van De Vorst, A., "Alteration of Guanine Residues During Proflavine Mediated Photosensitization of DNA," Photochemistry and Photobiology vol. 33, (1981) pp. 325-333.

Piette, J. Calberg-Bacq, C.M., and Van De Vorst, A., "Production of Breaks in Single and Double-Stranded Forms of Bacteriophage $_\phi$X174 DNA by Proflavine and Light Treatment," Photochemistry and Photobiology vol. 30, (1979) pp. 369-378.

Speck, William T., Rosenkranze, Samual, Rosenkranze, Herbert S., "Further Observations on the Photooxidation of DNA in the Presence of Riboflavin," Biochimica et Biophysica Acta, 435 (1976) pp. 39-44.

Tsugita, Akira, Okada, Yoshiko and Uehara, Kihachiro, "Photosensitized Inactivation Of Ribonucleic Acids In The Presence Of Ribflavin," Biochim. Biophys. Acta, 360-363 (1965).

Belikov et al., "Choice of an Effective Method of Analysis of Riboflavin and Study of its Stability" (1988) Farmatsiya, 37(2), 39-41, in DRUGU, AN 1988-39621.

Way et al., "HPLC Analysis of Riboflavin and its Photodegradation Products in an intravenous infusions Formulation" (1990) Pharm. Res., 7(9), Suppl., S26, in DRUGU, AN 1991-11544.

Ramu t al. "The Riboflavin-Mediated Photooxidation of Doxorubicin" (2000) Cancer Chemother. Pharmacol., 46(6), 449-458.

Friedman, L.I. et al., (1995), "Reducing the infectivity of blood components—what we have learned", Immun. Invest. 24(1&2):49-71.

Ghiron, C.A. and Spikes, J.D., (1965), "The flavin-sensitized photoinactivation of trypsin", Photochem. and Photobio. 4:13-26.

Hanson, C.V., (Mar. 1979), "Photochemical Inactivation of Deoxyribonucleic and Ribonucleic Acid Viruses by Cholorpromazine", Antimicrob. Agent Chemother, 15(3):461-464.

Hoffman, M.E. and Meneghini, R., (1979), "DNA strand breaks in mammalian cells exposed to light in the presence of riboflavin and tryprophan", Photochem. and Photobio. 29:299-303.

Malik et al., (1990), "New trends in photobiology—bactericidal effects of photoactivated porphyrins—an alternative approach to antimicrobial drugs", J. Photochem. Photobiol. Pt. B:Biology, 5:281-293.

North et al. ((993), "Photosensitizers as Virucidal Agents", J. Photobiol, 17(2):99-108.

Kabuta, H. et al., "Inactivation of viruses by dyes and visible light,"(1978) Chemical Abstracts 87(1), Abstract No. 400626.

Kale, H. et al., "Assessment of the genotoxic potential of riboflavin and lumiflavin; B. Effect of light," (1992) Mutation Research 298:17-23.

Friedman, L.I. et al., "Reducing the infectivity of blood components—what we have learned," (1995) Immunological Investigations 24(1&2):49-71.

Ghiron, C.A. and Spikes, J.D., "The flavin-sensitized photoinactivation of trypsin," (1965) Photochemistry and Photobiology 4:13-26.

Hoffmann, M.E. and Meneghini, R., "DNA strand breaks in mammalian cells exposed to light in the presence of riboflavin and tryptophan," (1979) Photochemistry and Photobiology 29:299-303.

Abdurashidova, G.G. et al., "Polynucleotide-protein itneractions in the translation system. Identification of proteins itneracting with tRNA in the A- and P-sites of E. coli ribosomes," (1979) Nucleic Acids Res. 6(12):3891-3909.

Budowsky, E.I. et al., "Induction of polynucleotide-protein cross-linkages by ultraviolet irradiation," (1986) Eur. J. Biochem. 159:95-101.

Budowsky, E.I. and Abdurashidova, G.G., "Polynucleotide-Protein Cross-Links Induced by Ultraviolet Light and Their Use for Structural Investigation of Nucleoproteins," (1989) Progress in Nucleic Acid Res. and Mol. Biol. 37:1-65.

Budowsky, E.I., "Problems and Prospects for Preparation of Killed Antiviral Vaccines," (1991) Adv. Virus Res. 39:255-290.

Budowsky, E.I. et al., "Principles of selective inactivation of viral genome. VI. Inactivation of the infectivity of the influenza virus by the action of β-propiolactone," (1991) Vaccine 9:398-402.

Budowsky, E.I. et al., "Principles of selective inactivation of viral genome. VII. Some peculiarities in determination of viral suspension infectivity during inactivation by chemical agents," (1991) Vaccine 9:473-476.

Budowsky, E.I. et al., "Principles of selective inactivation of viral genome. VIII. The influence of β-propiolactone on immunogenic and protective activities of influenza virus," (1993) Vaccine 11(3):343-348.

Budowsky, E.I. et al., "Preparation of cyclic 2',3'-monophosphates of oligoadenylates (A2'p),A>p and A3'p(A2'p).,A>p," (1994) Eur. J. Biochem. 220:97-104.

Cadet, J. et al., "Mechanisms and Products of Photosensitized Degradation of Nucleic Acids and Related Model Compounds," (1983) Israel J. Chem. 23:420-429.

Goodrich, R.P. and Platz, M.S., "The design and development of selective, photoactivated drugs for sterilization of blood products," (1997) Drugs of the Future 22(2):159-171.

Hoffman, M.E. and Meneghini, R., "DNA Strand Breaks in Mammalian Cells Exposed to Light in the Presence of Riboflavin and Tryptophan," (1979) Photochemistry and Photobiology 29:299-303.

Ivanchenko, V.A. et al., "The photochemistry of purine components of nucleic acids. I. The efficiency of photolysis of adenine and guanine derivatives in aqueous solution," (1975) *Nucleic Acids Res.* 2(8):1365-1373.

Korycka-Dahl, M. and Richardson, T., "Photodegradation of DNA with Fluorescent Light in the Presence of Riboflavin, and Photoprotection by Flavin Triplet-State Quenchers," (1980) *Biochemica et Biophysica Acta* 610:229-234.

Kovalsky, O.I. and Budowsky, E.I., "Laser (Two-Quantum) Photolysis of Polynucleotides and Nucleoproteins: Quantitative Processing of Results," 1990, *Photochemistry and Photobiology* 5(6):659-665.

Kuratomi, K. and Kobayashi, Y., "Studies on the Interactions Between DNA and Flavins," (1977) *Biochemica et Biophysica Acta* 476:207-217.

Peak, J.G. et al., "DNA Breakage Caused by 334-nm Ultraviolet Light is Enhanced by Naturally Occurring Nucleic Acid Components and Nucleotide Coenzymes," (1984) *Photochemistry and Photobiology* 39(5):713-716.

Piette, J. et al., "Alteration of Guanine Residues During Proflaving Mediated Photosensitization of DNA," (1981) *Photochemistry and Photobiology* 33:325-333.

Piette, J. et al., "Production of Breaks in Single- and Double-Stranded Forms of Bacteriophage φX174 DNA by Proflavine and Light Treatment," (1979) *Photochemistry and Photobiology* 30:369-378.

Simukova, N.A. and Budowsky, E.I., "Conversion of Non-Covalent Interactions in Nucleoproteins into Covalent Bonds: UV-Induced Formation of Polynucleotide-Protein Crosslinks in Bacteriophage Sd Virions," (1974) *FEBS Letters* 38(3):299-303.

Speck, W.T. et al., "Further Observations on the Photooxidation of DNA in the Presence of Riboflavin," (1976) *Biochimica et Biphysica Acta* 435:39-44.

Tsugita, A. et al., "Photosensitized inactivation of ribonucleic acids in the presence of riboflavin," (1965) *Biochim. Biophys. Acta* 103:360-363.

Webb, R.B. and Malina, M.M., "Mutagenesis in *Escherichia coli* by Visible Light," (1967) *Science* 156:1104-1105.

Ennever, J.F. and Speck, W.T., "Short Communication. Photochemical Reactions of Riboflavin: Covalent Binding to DNA and to Poly (dA)•Poly (dT)," (1983) *Pediatr. Res.* 17:234-236.

Matthews, J.L. et al., "Photodynamic therapy of viral contaminants with potential for blood banking applications," (1988) *Transfusion* 28(1):81-83.

Brodie, A.F. and Watanabe, T., "Mode of action of vitamin K in microorganisms," (1966) *Vitam. Horm.* 24:447-463.

Chow, C.S. and Barton, J.K., "Recognition of G-U mismatches by tris(4,7-diphenyl-1,10-phenanthroline)rhodium(III)," (1992) *Biochemistry* 31(24):5423-5429.

Deutsch, E., "Vitamin K in medical practice: adults," (1966) *Vitam. Horm.* 24:665-680.

Joshi, P.C., "Comparison of the DNA-damaging property of photosensitized riboflavin via singlet oxygen ($^1O_2$) and superoxide radical ($O_i^-$) mechanisms," (1985) *Toxicology Letters* 26:211-217.

Klebanoff, M.A. et al., "The risk of childhood cancer after neonatal exposure to vitamin K," (1993) *New Eng.. J. Med.* 329(13):905-908.

Korycka-Dahl, M. and Richardson, T., "Photodegradation of DNA with fluorescent light in the presence of riboflavin, and photoprotection by flavin triplet-state quenchers," (1980) *Biochimica et Biophysica Acta* 610:229-234.

Leontis, N.B. and Westhof, E., "The 5S rRNA loop E: chemical probing and phylogenetic data versus crystal structure," (1998) *RNA* 4:1134-1153.

Lim, A.C. and Barton, J.K., "Chemical probing of tDNA$^{Phe}$ with transition metal complexes: a structural comparison of RNA and DNA," (1993) *Biochemistry* 32:11029-11034.

Maddox, J., "The working of vitamin K," (1991) *Nature* 353(6346):695.

McCord, E.F., "Chemically induced dynamic nuclear polarization studies of yeast," (1984) *Biochemistry* 23:1935-1939.

Merenstein, G.B. et al. (Vitamin K Ad Hoc Task Force), "Controversies concerning vitamin K and the newborn," (1993) *Pediatrics* 91(5):1001-1003.

Merrifield, L.S. and Yang, H.Y., "Factors affecting the antimicrobial activity of vitamin K5," (1965) *Appl. Microbiol.* 13(5):766-770.

Merrifield, L.S. and Yang, H.Y., "Vitamin K5 as a fungistatic agent," (1965) *Applied Microbiol.* 13(5):660-662.

Murata, A. et al., "Effect of vitamins other than vitamin C on viruses: virus-inactivating activity of vitamin K5," (1983) *J. Nutr. Sci. Vitaminol (Tokyo)* 29(6):721-724.

Naseem, I. et al., "Effect of alkylated and intercalated DNA on the generation of superoxide anion by riboflavin," (1988) *Bioscience Reports* 8(5):485-492.

Pratt, R. et al., "Vitamin $K_5$ as an Antimicrobial Medicament and Preservative," (1950) *J. Am. Pharm. Ass'n* 39(3):127-134.

Shwartzman, G., "Antibacterial Properties of 4-Amino-2-Methyl-1-Naphthol Hydrochloride," (1948) *Proc. Soc. Exp. Biol. Med.* 67:376-378.

Spranger, J., "Does vitamin K cause cancer?" (1993) *Eur. J. Pediatr.* 152(2):174.

Vest, M., "Vitamin K in medical practice: pediatrics," (1966) *Vitam. Horm.* 24:649-663.

Yang, H.Y. et al., "Vitamin $K_5$ as a Food Preservative," (1958) *Food Technology* 501-504.

Akompong, T., et al. Gametocytocidal Activity and Synergistic Interactions of Riboflavin with Standard Antimalarial Drugs against Growth of *Plasmodium falciparum*. In Vitro. *Antimicrob Agents Chemother*, Nov. 2000; 44:3107-3111.

Akompong, T., et al., In Vitro Activity of Riboflavin against the Human Malaris Parasite *Plasmodium falciparum*, *Antimicrobial Agents and Chemotherapy*, Jan. 2000, p. 88-96, vol. 44, No. 1.

Appleyard, "Photosensitivity of Semliki forest and other viruses" *Journal of General Virology*, vol. 1, 1967 pp. 143-152.

Boyd RF. "Basic Medical Microbiology," 1995; *Clinical Parasitology*, Boston Little, Brown and Company :513-514.

Das BS, et al. "Riboflavin deficiency and severity of malaria" *Eur J Clin Nutr*, Apr. 1988;42:277-83.

Dodd, R.Y. "Transmission of Parasites by Blood Transfusion" *Vox Sanguinis* 1998; 74 (Suppl 2): 161-163.

Dutta P. "Enhanced uptake and metabolism of riboflavin in erythrocytes infected with Plasmodium falciparum" *J Protozool* Sep.-Oct. 1991;38:479-83.

Francki, et al., "Classification and nomenclature of viruses, Fifth report of the international committee on taxonomy of viruses. Archives of virology Supplementum 2", Springer-Verlag, Wien New-York, p. 216-232.

Gottlieb, P., et al., Inactivation of Trypanosoma cruzi Trypomastigote Forms in Blood Components by Photodynamic Treatment with Phthalocyanines, *Photochemistry and Photobiology*; vol. 62. No. 5, pp. 869-874, 1995.

Gottlieb, P., et al., "Inactivation of Trypanosoma cruzi Trypomastigote Forms in Blood Components with a Psoralen and Ultraviolet A Light" *Photochemistry and Photobiology*, 1996, 63(5): 562-565.

Kobayashi et al., The molecular mechanism of mutation. Photodynamic action of flavins on the RNA-synthesizing system, (1983), Chemical Abstracts 98(1) Abstract No. 1200.

Nahlen, B.L., et al., Reassessment of blood donor selection criteria for United States travelers to malarious areas, *Transfusion*, 1991-vol. 31, No. 9, p. 798-804.

Ponnudurai, T., et al., The production of mature gametocytes of Plasmodium falciparum in continuous cultures of different isolates infective to mosquitoes, *Transactions of the Royal Society of Tropical Medicine and Hygiene*, vol. 76, No. 2, 1982.

Ramirez, L.E., et al., Prevention of transfusion-associated Chagas' disease by sterilization of *Trypanosoma cruzi*-infected blood with gentian violet, ascorbic acid, and light. *Transfusion*, 1995-vol. 35, No. 3, p. 226-230.

Shulman I. "Transmission of parasitic infections by blood transfusion" *Principles of transfusion medicine eds.* EC. Rossi, TL. Simon, GL. Moss, SA. Gould, 1996; 733-8.

Soliman, et al., "Applicant of an immunoperoxidase monolyer assay for the detection of arboviral antibodies", *Journal of Virological Methods*, vol. 65, No. 2, 1997, pp. 147-151.

Trager, W., et al., "Human Malaris Parasites in Continuous Culture" *Science*, vol. 193, (Aug. 1976) p. 673-675.

Ultracure 100SS Plus Specifications, EFOS USA, Inc., Williamsville, NY, USA, product advertisement.

White, N.J., "The Treatment of Malaria" *The New England Journal of Medicine*, vol. 335, No. 11, (Sep. 1996) p. 800-806.

* cited by examiner

WNV Reduction for Plasma Treatment

FIGURE 5

INACTIVATION OF WEST NILE VIRUS AND MALARIA USING PHOTOSENSITIZERS

CROSS-REFERENCE TO RELATED APPLICATIONS

This application claims priority to U.S. provisional application 60/353,162, filed Feb. 1, 2002, and is a continuation-in-part of U.S. application Ser. No. 09/586,147, filed Jun. 2, 2000, now abandoned, which is a continuation-in-part of U.S. application Ser. No. 09/357,188 filed Jul. 20, 1999, now U.S. Pat. No. 6,277,337, which is a continuation-in-part of U.S. application Ser. No. 09/119,666 filed Jul. 21, 1998, now U.S. Pat. No. 6,258,577 which are hereby incorporated by reference to the extent not inconsistent with the disclosure herewith.

BACKGROUND OF THE INVENTION

Contamination of blood supplies with infectious microorganisms such as malaria, West Nile virus, HIV, hepatitis and other viruses and bacteria presents a serious health hazard for those who must receive transfusions of whole blood or administration of various blood components such as platelets, red cells, blood plasma, Factor VIII, plasminogen, fibronectin, anti-thrombin III, cryoprecipitate, human plasma protein fraction, albumin, immune serum globulin, prothrombin complex, plasma growth hormones, and other components isolated from blood. Blood screening procedures may miss contaminants, and sterilization procedures which do not damage cellular blood components but effectively inactivate all infectious viruses and other microorganisms have not heretofore been available. In addition, a system that uses the same chemistry to inactivate microorganisms in different fluids, for example separate blood components, is desired for many reasons, including ease of use in a blood bank setting. This type of system has not heretofore been available. It is also desired that the inactivation treatment be easily implemented in a blood bank setting, and produce inactivation in a short period of time.

Malaria is an infectious disease caused by protozoan parasites of the *Plasmodium* genera. The species that cause malaria in humans are: *P. falciparum* (most malignant), *P. vivax*, *P. malariae*, and *P. ovale* (Mims, C A, et al. *Medical Microbiology* 1993; London: Mosby: 30.8–30.9). *Plasmodium* parasites are spread by the female anopheles mosquito, which transmits the infection to various primates and to non-immune human hosts (Boyd R F. Clinical parasitology. In *Basic Medical Microbiology*, 1995; Boston: Little, Brown and Company:513–514). Donated blood is not tested for infection with malaria, although there are no means to completely prevent the transmission of malaria by blood transfusion (Shulman I. Transmission of parasitic infections by blood transfusion. In *Principles of transfusion medicine*, eds. E C. Rossi, T L. Simon, G L. Moss, S A. Gould, 1996; Baltimore: Williams and Wilkins:733–8). In the United States, the risk of transfusion-transmitted malaria is limited by excluding blood donors who have traveled to malaria-endemic areas. This results in the deferral of 70,000 donors a year (Nahlen B L, et al. Reassessment of blood donor selection criteria for United States travelers to malarious areas. *Transfusion*. 1991; 31:798–804). In countries with a high prevalence of malaria infection, deferral of donors may not be an option. A method for the inactivation of malaria parasites in blood may mitigate the risk of transfusion transmission from donors that are not removed through ordinary screening methods, and may allow the military to use donors that had been stationed in malaria-endemic areas. Such a method may also reduce the risk of transfusion-transmitted malaria in countries where large portions of the donor population have been exposed to the parasite.

West Nile Virus has recently entered the United States and causes a variety of illnesses, including West Nile encephalitis, West Nile meningitis and West Nile meningoencephalitis. West Nile virus is transmitted through mosquitoes and birds. West Nile virus is known to be transmitted through transfusion of blood products from infected individuals (<http://www.cdc.gov/ncidod/dvbid/westnile/qa/transfusion.htm>). Currently, blood is not tested for West Nile virus and exclusion of donors who are believed to be infected with the West Nile Virus is the only method used to prevent the spread of West Nile virus through blood transfusions. However, most people who are infected with the West Nile Virus do not show symptoms and may not be excluded from the donation process, therefore, transmitting the virus through transfused blood.

There are several reported methods of decontaminating blood. Solvent detergent methods of blood component decontamination work by dissolving phospholipid membranes surrounding viruses such as HIV, and do not damage protein components of blood; however, if blood cells are present, such methods cannot be used because of damage to cell membranes.

The use of photosensitizers, compounds which absorb light of a defined wavelength and transfer the absorbed energy to an energy acceptor, has been proposed for blood component sterilization. For example, European Patent application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red and methylene blue, as blood additives. Protoporphyrin, which occurs naturally within the body, can be metabolized to form a photosensitizer; however, its usefulness is limited in that it degrades desired biological activities of proteins. Chlorpromazine is also exemplified as one such photosensitizer; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159–171 provides a review of some photosensitizers including psoralens, and some of the issues of importance in choosing photosensitizers for decontamination of blood products. The use of texaphyrins for DNA photocleavage is described in U.S. Pat. No. 5,607,924 issued Mar. 4, 1997 and U.S. Pat. No. 5,714,328 issued Feb. 3, 1998 to Magda et al. The use of sapphyrins for viral deactivation is described in U.S. Pat. No. 5,041,078 issued Aug. 20, 1991 to Matthews, et al. Inactivation of extracellular enveloped viruses in blood and blood components by Phenthiazin-5-ium dyes plus light is described in U.S. Pat. No. 5,545,516 issued Aug. 13, 1996 to Wagner. The use of porphyrins, hematoporphyrins, and merocyanine dyes as photosensitizing agents for eradicating infectious contaminants such as viruses and protozoa from body tissues such as body fluids is disclosed in U.S. Pat. No. 4,915,683 issued Apr. 10, 1990 and related U.S. Pat. No. 5,304,113 issued Apr. 19, 1994 to Sieber et al. The mechanism of action of such photosensitizers is described as involving preferential binding to domains in lipid bilayers, e.g. on enveloped viruses and some virus-infected cells. Photoexcitation of membrane-bound agent molecules leads to the formation of reactive oxygen species such as singlet oxygen which causes lipid peroxidation. A problem with the use of such photosensitizers is that they attack cell membranes of desirable components of fluids to be decontaminated, such as red blood cells, and the singlet oxygen also attacks desired protein components of fluids being treated. U.S. Pat. No. 4,727,027 issued Feb. 23, 1988 to Wiesehahn, G. P., et al. discloses the use of furocoumarins including psoralen and derivatives for decontamination of blood and blood products, but teaches that steps must be taken to reduce the availability of dissolved oxygen and other reactive species in order to inhibit denaturation of biologically active proteins.

Photoinactivation of viral and bacterial blood contaminants using halogenated coumarins is described in U.S. Pat. No. 5,516,629 issued May 14, 1996 to Park, et al. U.S. Pat. No. 5,587,490 issued Dec. 24, 1996 to Goodrich Jr., R. P., et al. and U.S. Pat. No. 5,418,130 to Platz, et al. disclose the use of substituted psoralens for inactivation of viral and bacterial blood contaminants. The latter patent also teaches the necessity of controlling free radical damage to other blood components. U.S. Pat. No. 5,654,443 issued Aug. 5, 1997 to Wollowitz et al. teaches new psoralen compositions used for photodecontamination of blood. U.S. Pat. No. 5,709,991 issued Jan. 20, 1998 to Lin et al. teaches the use of psoralen for photodecontamination of platelet preparations and removal of psoralen afterward. U.S. Pat. No. 5,120,649 issued Jun. 9, 1992 and related U.S. Pat. No. 5,232,844 issued Aug. 3, 1993 to Horowitz, et al., also disclose the need for the use of "quenchers" in combination with photosensitizers which attack lipid membranes, and U.S. Pat. No. 5,360,734 issued Nov. 1, 1994 to Chapman et al. also addresses the problem of prevention of damage to other blood components.

Photosensitizers which attack nucleic acids are known to the art. U.S. Pat. No. 5,342,752 issued Aug. 30, 1994 to Platz et al. discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. This patent fails to disclose an apparatus for decontaminating blood on a flow-through basis. U.S. Pat. No. 5,798,238 to Goodrich, Jr., et al., discloses the use of quinolone and quinolone compounds for inactivation of viral and bacterial contaminants.

Binding of DNA with photoactive agents has been exploited in processes to reduce lymphocytic populations in blood as taught in U.S. Pat. No. 4,612,007 issued Sep. 16, 1986 and related U.S. Pat. No. 4,683,889 issued Aug. 4, 1987 to Edelson.

Riboflavin (7,8-dimethyl-10-ribityl isoalloxazine) has been reported to attack nucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360–363; and Speck, W. T. et al. (1976), "Further Observations on the Photooxidation of DNA in the Presence of Riboflavin," Biochimica et Biophysica Acta 435:39–44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207–217. Hoffmann, M. E., et al. (1979), "DNA Strand Breaks in Mammalian Cells Exposed to Light in the Presence of Riboflavin and Tryptophan," Photochemistry and Photobiology 29:299–303 describes the use of riboflavin and tryptophan to induce breaks in DNA of mammalian cells after exposure to visible fluorescent light or near-ultraviolet light. The article states that these effects did not occur if either riboflavin or tryptophan was omitted from the medium. DNA strand breaks upon exposure to proflavine and light are reported in Piette, J. et al. (1979), "Production of Breaks in Single- and Double-Stranded Forms of Bacteriophage ΦX174 DNA by Proflavine and Light Treatment," Photochemistry and Photobiology 30:369–378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325–333.

J. Cadet, et al. (1983), "Mechanisms and Products of Photosensitized Degradation of Nucleic Acids and Related Model Compounds," Israel J. Chem. 23:420–429, discusses the mechanism of action by production of singlet oxygen of rose bengal, methylene blue, thionine and other dyes, compared with mechanisms not involving production of singlet oxygen by which nucleic acid attack by flavin or pteron derivatives proceeds. Riboflavin is exemplified in this disclosure as having the ability to degrade nucleic acids. Korycka-Dahl, M., et al. (1980), "Photodegradation of DNA with Fluorescent Light in the Presence of Riboflavin, and Photoprotection by Flavin Triplet-State Quenchers," Biochimica et Biophysica Acta 610:229–234 also discloses that active oxygen species are not directly involved in DNA scission by riboflavin. Peak, J. G., et al. (1984), "DNA Breakage Caused by 334-nm Ultraviolet Light is Enhanced by Naturally Occurring Nucleic Acid Components and Nucleotide Coenzymes," Photochemistry and Photobiology 39:713–716 further explores the mechanism of action of riboflavin and other photosensitizers. However, no suggestion is made that such photosensitizers be used for decontamination of medical fluids.

Addition of riboflavin to in vitro cultures of *P. falciparum* has been reported to inhibit asexual parasite growth (Akompong, T., et al. In Vitro Activity of Riboflavin against the Human Malaria Parasite *Plasmodium falciparum., Antimicrob Agents Chemother*, January 2000; 44: 88–96) and kill gametocytes (Akompong, T., et al. Gametocytocidal Activity and Synergistic Interactions of Riboflavin with Standard Antimalarial Drugs against Growth of *Plasmodium falciparum* In Vitro. *Antimicrob Agents Chemother*, November 2000; 44: 3107–3111). Riboflavin, when added to cultures in the asexual stage in combination with antimalarial drugs, was reported to enhance the drug activity (Akompong, T., et al. Gametocytocidal Activity and Synergistic Interactions of Riboflavin with Standard Antimalarial Drugs against Growth of *Plasmodium falciparum* In Vitro. *Antimicrob Agents Chemother*, November 2000; 44: 3107–3111). In earlier works (Das B S, et al. Riboflavin deficiency and severity of malaria, *Eur J Clin Nutr*, 1988 April; 42:277–83; Dutta P. Enhanced uptake and metabolism of riboflavin in erythrocytes infected with *Plasmodium falciparum. J Protozool* 1991 September–October; 38:479–83), riboflavin deficiency was observed to be detrimental to the parasite. The use of riboflavin as a photosensitizer to treat blood and blood components that may have malaria infection has not been reported.

Apparatuses for decontamination of blood have been described in U.S. Pat. No. 5,290,221 issued Mar. 1, 1994 to Wolfe, Jr., et al. and U.S. Pat. No. 5,536,238 issued Jul. 16, 1996 to Bischof. U.S. Pat. No. 5,290,221 discloses the irradiation of fluid in a relatively narrow, arcuate gap. U.S. Pat. No. 5,536,238 discloses devices utilizing optical fibers extending into a filtration medium. Both patents recommend as photosensitizers benzoporphryin derivatives which have an affinity for cell walls.

U.S. Pat. No. 5,527,704 issued Jun. 18, 1996 to Wolf, Jr., et al. discusses an apparatus to inactivate viruses contained in a body fluid in a container using methylene blue as a photosensitizer. The body fluid is maintained in a static state within the container during irradiation. U.S. Pat. No. 5,868,695 issued Feb. 9, 1999 to Wolf, Jr. et al. discloses a system where blood containing a photoactive material is directed in a predetermined flow path such as a serpentine in a narrow gap in a treatment chamber. PCT published application No. WO 96/06647 discloses irradiating a product in an array of light emitting diodes surrounded by a fluid used to prevent overheating of the diodes. Riboflavin and UV light inactivate viruses and bacteria in plasma and platelet products (Samar, R, et al. Poster, Viral Inactivation in Plasma Using Riboflavin-Based Technology. AABB 54$^{th}$ Annual Meeting. November 2001; Goodrich R P. The use of riboflavin for the inactivation of pathogens in blood products. *Vox Sang.* 2000; 78 (suppl 2):211–15). Riboflavin and visible light provide demonstrated virus inactivation in platelets (Goodrich, L, et al. Poster. Riboflavin Pathogen Inactivation Process Yields Good Platelet Cell Quality and Expedient Viral Kill. ASH 43$^{rd}$ Annual Meeting. December 2001) and in red cell suspensions (McAteer M J, et al. Poster: Photo-inactivation of virus in packed red blood cell units using riboflavin and visible light. AABB 53$^{rd}$ Annual Meeting. November 2000).

Sterilization procedures which do not damage cellular blood components but effectively inactivate infectious viruses and other microorganisms and contaminants are disclosed in U.S. Pat. Nos. 6,258,577, 6,277,337, 6,268,120 and PCT publications WO 01/28599, WO 00/04930. Storage solutions containing photosensitizers are disclosed in U.S. patent application Ser. No. 09/725,426 and U.S. patent application Ser. No. 09/596,429.

There is a need for an inactivation procedure for West Nile virus and malaria, as well as other microorganisms that are not detected in blood products.

All references, publications, patents and patent applications referred to herein are hereby incorporated by reference to the extent not inconsistent with the disclosure herewith.

SUMMARY OF THE INVENTION

Methods and apparatuses are provided for treating a fluid to inactivate at least some of the microorganisms that may be present therein or thereon, said fluid containing one or more components selected from the group consisting of protein, (e.g. biologically active protein such as a therapeutic protein), blood and blood constituents. One such method comprises mixing an inactivation-effective, substantially non-toxic amount of an endogenous photosensitizer or endogenously-based derivative photosensitizer with said fluid; and exposing said fluid to photoradiation of sufficient wavelength and energy to activate the photosensitizer, whereby said microorganisms are inactivated. In one particular embodiment, at least one type of parasite or virus is inactivated. In another particular embodiment, at least one type of non-screened microorganism is inactivated. In another particular embodiment, viruses and parasites are inactivated in the same process (i.e., when both are present in the same fluid).

Also provided is an apparatus for inactivating microorganisms which may be present in a fluid with an endogenous or endogenously-based derivative photosensitizer, comprising:

(a) a source of light that emits light of a suitable wavelength and intensity to activate the endogenous or endogenously-based derivative photosensitizer;

(b) means for maintaining the fluid and an effective amount of an endogenous or endogenously-based derivative photosensitizer in the light path for a sufficient time to achieve the desired level of inactivation.

The means for maintaining the fluid and an effective amount of an endogenous or endogenously-based derivative photosensitizer in the light path may comprise a support surface substantially parallel to said source of light; a cuvette or bag; or other means known in the art.

Also provided is a system for treating a fluid to inactivate microorganisms which may be present therein with an endogenous or endogenously-based derivative photosensitizer comprising: a container comprising said fluid, at least an effective amount of an endogenous photosensitizer or endogenously-based derivative photosensitizer, and optionally one or more additives, said container having a photopermeable surface sufficient to allow exposure of the fluid therein to an amount of photoradiation sufficient to activate the photosensitizer; at least one photoradiation source in light communication with said container, said source capable of generating a suitable wavelength and intensity to activate the endogenous photosensitizer or endogenously-based derivative photosensitizer whereby microorganisms present are inactivated.

Other systems, methods and apparatuses are provided, including a flow-through system for inactivation of microorganisms in a fluid containing such microorganisms comprising:

(a) means for mixing an effective amount of an endogenous photosensitizer or endogenously-based derivative photosensitizer with said fluid;

(b) a photopermeable container for said fluid in fluid communication with said means for adding photosensitizer;

(c) means for producing said selected flow rate of said fluid through said container; and (d) at least one photoradiation source for providing sufficient photoradiation to the fluid in said container of a type and amount selected to activate the photosensitizer.

Also provided is a stand-alone or batch-wise system for treating a fluid to inactivate microorganisms which may be present therein comprising:

(a) a photosensitizer in powdered form;

(b) a photopermeable container for containing said fluid and photosensitizer;

(c) means for agitating said container;

(d) at least one photoradiation source in light communication with said container, said source capable of providing sufficient photoradiation to the fluid in said container of a type and amount selected to activate the photosensitizer whereby microorganisms are inactivated.

The photopermeable container may be a transparent plastic bag, a transparent plastic container with rigid walls, or other containers as known to the art. The agitation may be provided by a shaker table, or other means for agitating known to the art.

Also provided is a method for collecting a fluid with reduced levels of microorganisms that may be present therein, said fluid containing one or more members of the group consisting of: blood and blood components, comprising:

(a) placing said fluid in a photopermeable container;

(b) adding an endogenous or endogenously-based derivative photoactive material;

(c) exposing said fluid to radiation of a sufficient wavelength and intensity to inactivate microorganisms which may be present in said blood or blood component.

Also provided is an apparatus for collecting a fluid with reduced levels of microorganisms that may be present therein, said fluid containing one or more members of the group consisting of: blood and blood components, comprising:

(a) a photopermeable container containing an endogenous or endogenously-based derivative photoactive material;

(b) a light source that emits light of a suitable wavelength and intensity to inactivate microorganisms which may be present in said fluid.

The photosensitizer may be a photo-activatable compound whose photolytic products (if any) are of low or no toxicity to humans or animals. The most preferred photosensitizer is 7,8-dimethyl-10-ribityl isoalloxazine. Other preferred photosensitizers are endogenous alloxazine or isoalloxazine photosensitizers. The photosensitizer is preferably a nucleic-acid-targeted non toxic photoactivatable compound which does not produce toxic photolytic breakdown products. Preferred photosensitizers are not porphyrin.

Photoradiation may comprise light in the visible spectrum, the ultraviolet spectrum, or light in both the visible and ultraviolet spectra. Any suitable wavelength or wavelengths of light may be used in any proportion and energy that produces the desired level of inactivation of microorganisms. As used herein, "wavelength" does not necessarily mean one discrete wavelength. Wavelength may comprise a range of about ±100 nm centered around one wavelength. Preferably, if ultraviolet light is used, the amount of ultraviolet light is kept to a level that minimizes damage to desired fluid components. Generally, this is provided by using 50% or less ultraviolet light relative to the total light energy delivered. Also, the wavelengths of light may be centered around one peak wavelength (i.e., a range of ±10 nm centered around one wavelength).

The fluid containing the photosensitizer is exposed to photoradiation of the appropriate wavelength to activate the photosensitizer, using an amount of photoradiation sufficient to activate the photosensitizer as described herein, but less than that which would cause non-specific damage to the biological components or substantially interfere with biological activity of other proteins present in the fluid. The wavelength used will depend on the photosensitizer selected and composition of the fluid, as is known to the art or readily determinable without undue experimentation following the teachings disclosed herein. Non-specific damage is damage that damages all components.

The photoradiation in both the ultraviolet and visible spectra may be supplied concurrently or sequentially, with the visible portion preferably being supplied first. The photoradiation source may be a simple lamp or may consist of multiple lamps radiating at differing wavelengths. The photoradiation source should be capable of delivering a sufficient amount of light to activate the photosensitizer, preferably from about 1 to at least about 200 $J/cm^2$, most preferably around 7 $J/cm^2$. All values and ranges of power are included herein.

As used herein, the term "inactivation of a microorganism" means totally or partially preventing the microorganism from replicating, either by killing the microorganism or otherwise interfering with its ability to reproduce.

Microorganisms include viruses (both extracellular and intracellular), bacteria, bacteriophages, fungi, blood-transmitted parasites such as malaria, and protozoa. Exemplary viruses include acquired immunodeficiency (HIV) virus, hepatitis A, B and C viruses, sinbis virus, cytomegaloviris, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, West Nile virus and others known to the art. Bacteriophages include ΦX174, Φ6, λ, R17, $T_4$, and $T_2$. Exemplary bacteria include *P. aeruginosa, S. aureus, S. epidermis, L. monocytogenes, E. coli, K. pneumonia* and *S. marcescens*. One particular class of microorganisms is non-screened microorganisms—those microorganisms that are not screened by current blood banking processes. Some non-screened microorganisms include malaria and West Nile virus. One class of microorganisms include those transmitted by mosquitoes, including malaria and West Nile virus.

Materials which may be treated by the methods of this invention include any materials which are adequately permeable to photoradiation to provide sufficient light to achieve microorganism inactivation, or which can be suspended or dissolved in fluids which have such permeability to photoradiation. Examples of such materials are whole blood and aqueous compositions containing biologically active proteins derived from blood or blood constituents. Packed red cells, platelets and plasma (fresh or fresh frozen plasma) are exemplary of such blood constituents. In addition, therapeutic protein compositions containing proteins derived from blood, such as fluids containing biologically active protein useful in the treatment of medical disorders, e.g. factor VIII, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen streptokinase complex, ceruloplasmin, transferrin, haptoglobin, antitrypsin and prekallikrein may be treated by the decontamination methods of this invention. The activity of a biologically-active protein in said fluid is at a biologically-active level after said exposing step. A therapeutic protein present in said fluid remains able to perform a therapeutic function after the exposing step.

The term "biologically active" means capable of effecting a change in a living organism or component thereof. "Biologically active" with respect to "biologically active protein" as referred to herein does not refer to proteins which are part of the microorganisms being inactivated. Similarly, "non-toxic" with respect to the photosensitizers means low or no toxicity to humans and other mammals, and does not mean non-toxic to the microorganisms being inactivated. "Substantial destruction" of biological activity means at least as much destruction as is caused by porphyrin and porphyrin derivatives, metabolites and precursors which are known to have a damaging effect on biologically active proteins and cells of humans and mammals. Similarly, "substantially non-toxic" means less toxic than porphyrin, porphyrin derivatives, metabolites and precursors that are known for blood sterilization.

The term "blood product" as used herein includes blood constituents and therapeutic protein compositions containing proteins derived from blood as defined above. Fluids containing biologically active proteins other than those derived from blood may also be treated by the methods of this invention.

Decontamination methods of this invention using endogenous photosensitizers and endogenously-based derivative photosensitizers do not substantially destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid. So long as fluid components retain sufficient biological activity to be useful for their intended or natural purposes, their biological activities are not considered to be "substantially destroyed."

Photosensitizers are known to be useful for inactivating microorganisms. A "photosensitizer" is defined as any compound which absorbs radiation of one or more defined wavelengths and subsequently utilizes the absorbed energy to carry out a chemical process. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers of this invention may include compounds which preferentially adsorb to nucleic acids, thus focusing their photodynamic effect upon microorganisms and viruses with little or no effect upon accompanying cells or proteins. Other photosensitizers are also useful in this invention, such as those using singlet oxygen-dependent mechanisms. Most preferred are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof. When endogenous or endogenously-based derivative photosensitizers are used, particularly when such photosensitizers are not inherently toxic or do not yield toxic photoproducts after photoradiation, no removal or purification step is required after decontamination, and treated product can be directly returned to a patient's body or administered to a patient in need of its therapeutic effect.

Non-endogenous photosensitizers based on endogenous structures, such as those described in U.S. Pat. No. 6,268,120 are also useful and included. These non-endogenous photosensitizers and endogenously-based derivative photosensitizers are referred to herein as endogenously-based derivative photosensitizers.

Preferred photosensitizers (also referred to herein as "photoactivators") are endogenous alloxazines, K vitamins and vitamin L, specifically 7,8-dimethyl-10-ribityl isoalloxazine, (riboflavin) 7,8-dimethylalloxazine, 7,8,10-trimethylisoalloxazine, alloxazine mononucleotide, isoalloxazine-adenosine dinucleotide, and isoalloxazine derivatives and analogs as set forth in U.S. Pat. No. 6,268,120 and U.S. patent application Ser. No. 09/777,727, both of which are incorporated herein by reference to the extent not inconsistent herewith. Specifically, the terms "endogenously-based derivative photosensitizers" and "isoalloxazine derivative photosensitizers" are synonymous and mean compounds having the structure:

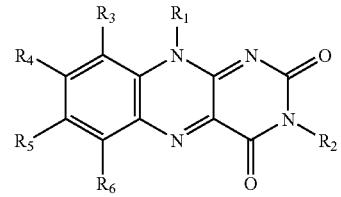

wherein $R_1$, $R_2$, $R_3$, $R_4$, $R_5$ and $R_6$ are, independently from one another, selected from the group consisting of hydrogen, optionally substituted hydrocarbyl, alcohol, amine, polyamine, sulfate, phosphate, halogen selected from the group consisting of chlorine, bromine and iodine, salts of the foregoing, and —$NR^a$—$(CR^bR^c)_n$—X wherein X is a halogen selected from the group consisting of chlorine, bromine and iodine, $R^a$, $R^b$ and $R^c$ are, independently of each other, selected from the group consisting of hydrogen, optionally substituted hydrocarbyl, and halogen selected from the group consisting of chlorine, bromine and iodine, and n is an integer from 0 to 20.

Preferred endogenously-based derivative photosensitizers are compounds having the structure:

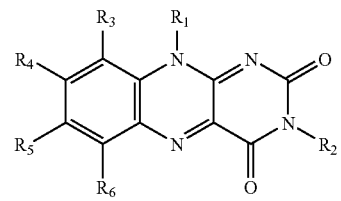

provided that $R_1$ is not —OH or a straight chain alkyl group where the second carbon of the chain is substituted with —OH or =O; and $R_1$, $R_4$, and $R_5$ are not all methyl groups when $R_2$, $R_3$, and $R_6$; are all hydrogen. In specifically exemplified classes of endogenously-based derivative photosensitizers, $R_1$ is not a 2-, 3-, 4- or 5-carbon straight chain alkyl that terminates in —OH, —COH, or —H when $R_2$, $R_3$ and $R_6$ are H, and $R_4$ and $R_5$ are $CH_3$; $R_1$ is not —$CH_2CH_2$—$(CHOH)_2$—$CH_3$ or —$CH_2CH_2$—$(CHOH)_2$—$CH_2SO_4$ or 1'-D-sorbityl or 1'-D-dulcityl or 1'-D-rhamnityl or 1'-D,L-glyceryl or —$CH_2$—O—C(O)—$CH_3$ or —$CH_2$—O—C(O)—$CH_2CH_3$ or 2', 3', 4', 5'-di-O-isopropyridene-riboflavin or 8-aminooctyl when $R_2$, $R_3$ and $R_6$ are H and $R_4$ and $R_5$ are $CH_3$; $R_1$ is not 1'-D-sorbityl or 1'-D-dulcityl when $R_4$ and $R_5$ are both chlorines and when $R_2$, $R_3$ and $R_6$ are all hydrogens; $R_5$ is not ethyl or chloro when $R_1$ and $R_4$ are methyl and $R_2$, $R_3$ and $R_6$ are all hydrogens; $R_4$ and $R_5$ are not both methoxy or both tetramethylene when $R_1$ is methyl and $R_2$, $R_3$ and $R_6$ are all hydrogens; $R_2$ is not —$CH_2CH_2NH$ when $R_1$, $R_4$ and $R_5$ are $CH_3$ and $R_3$ and $R_6$ are H; $R_2$ is not

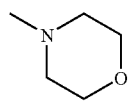

when $R_1$, $R_4$ and $R_5$ are $CH_3$ and $R_3$ and $R_6$ are H; $R_5$ is not chloro when $R_4$ is methoxy and $R_1$ is ethyl-2'N-pyrrolidino and $R_2$, $R_3$, and $R_6$ are hydrogen; $R_1$ is not N,N-dimethylaminopropyl or N,N-diethylaminoethyl when $R_5$ is chloro or methyl and $R_2$, $R_3$, $R_4$ and $R_6$ are hydrogen; $R_3$ is not $—NH(CH_2CH_2)Cl$ when $R_6$ is $—NH_2$ and $R_1$, $R_2$, $R_4$ and $R_5$ are H; $R_1$, $R_4$, $R_5$ are not all methyl groups when all of $R_2$, $R_3$ and $R_6$ are hydrogens; R1 and R2 are not both methyl groups when R3, R4, R5 and R6 are H; $R_1$, $R_4$, $R_5$ and $R_2$ are not all methyl groups when $R_3$ and $R_6$ are hydrogens; $R_2$ is not carboxymethyl when $R_1$, $R_4$ and $R_5$ are methyl and $R_3$ and $R_6$ are hydrogen; $R_4$ is not $—NH_2$ when $R_1$ and $R_5$ are methyl and $R_2$, $R_3$ and $R_6$ are all hydrogen; $R_1$ is not a phenyl group when $R_4$ and $R_5$ are methyl and $R_2$, $R_3$ and $R_6$ are all H; $R_1$ is not methyl or N,N-dimethylaminoethyl when all of $R_2$, $R_3$, $R_4$, $R_5$ and $R_6$ are hydrogen; $R_2$, $R_4$, $R_5$ are not all methyl when $R_1$ is acetoxyethyl and $R_3$ and $R_6$ are hydrogen; $R_5$ is not methyl when $R_1$ is N,N-diethylaminoethyl and $R_2$, $R_3$, $R_4$ and $R_6$ are all hydrogen; $R_4$ and $R_5$ are not both chlorine when $R_1$ is methyl and $R_2$, $R_3$ and $R_6$ are all hydrogen; $R_1$ is not ethyl, β-chloroethyl, n-butyl, anilino, benzyl, phenyl, p-tolyl or p-anisyl when $R_5$ is $NH_2$ and $R_2$, $R_3$, $R_4$ and $R_6$ are all hydrogen; and $R_4$ is not chlorine when $R_1$ is N,N-dimethylaminopropyl and $R_2$, $R_3$, $R_5$ and $R_6$ are all hydrogen.

In one group of compounds, n is an integer between 0 and 5. In another group of compounds, n is an integer from 0 to 10. In another group of compounds, n is an integer from 0 to 20.

Compounds containing any combination of substituents or members of the Markush groups specified above are within the scope of the invention. All compounds of the invention have the ability to neutralize microorganisms. All substituents of the compounds of the invention may be the same, all substituents may be different, or any combination of substituents may be the same or different. Substituents with a specified function, for example those that impart water solubility to the compound, may be included at any of $R_{1-6}$. Compounds of the invention include all those compounds with the isoalloxazine backbone (shown below):

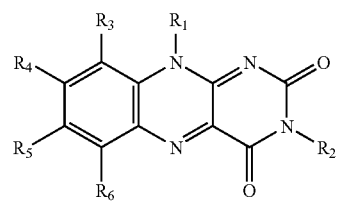

where $R_1$–$R_6$ are substituted with various substituents, as described elsewhere, except those previously known to the art. The substituents included in the compounds and used in the methods of the invention may be any substituent not having structures or reactivity which would substantially interfere with the desired microorganism neutralization of the microorganism neutralizer, as may readily be determined without undue experimentation by those skilled in the art.

The invention provides a class of compounds wherein one or a plurality of $R_1$, $R_2$, $R_3$, $R_4$, $R_5$ and $R_6$ are neither $CH_3$ nor H; and a class of compounds wherein one of $R_1$, $R_2$, $R_3$, $R_4$, $R_5$ and $R_6$ is neither $CH_3$ nor H. The invention also provides a class of compounds wherein one or a plurality of R1–R6 are $CH_3$ or H. Particular embodiments of compounds of those classes include those wherein a $R_1$, $R_2$, $R_3$, $R_4$, $R_5$ or $R_6$ which is neither $CH_3$ nor H imparts substantial water solubility to the microorganism neutralizer. Preferred examples of these compounds are:

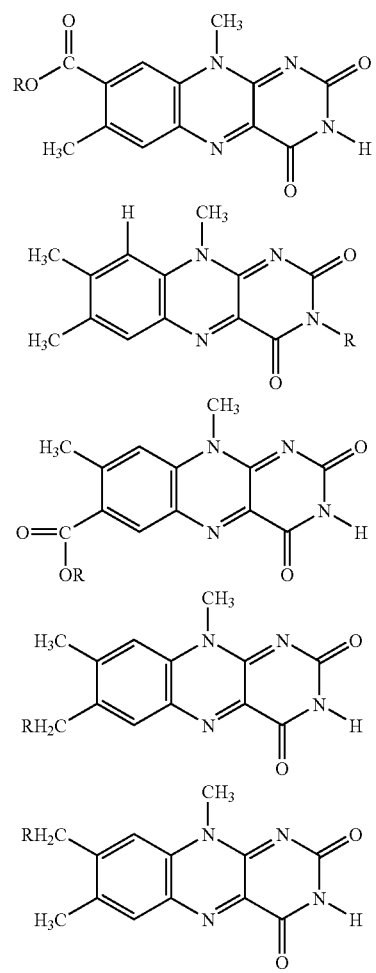

wherein R is a substituent imparting water solubility to the molecule, including, but not limited to, ascorbate, alcohol, polyalcohol; amine or polyamines, straight chain or cyclic saccharides, sulfates, phosphates, alkyl chains optionally substituted with —OH at any position, glycols, including polyethylene glycol and polyethers.

Another class of compounds of the invention include those wherein a $R_1$, $R_2$, $R_3$, $R_4$, $R_5$ or $R_6$ that is neither H nor $CH_3$ contains a halogen or is a halogen, wherein the halogen is selected from the group consisting of fluorine, chlorine, bromine and iodine. Particular embodiments of compounds of this class include compounds where a $R_1$, $R_2$, $R_3$, $R_4$, $R_5$ or $R_6$ that is neither H nor $CH_3$ is: $—NR^a—(CR^bR^c)_n—X$ wherein X is a halogen selected from the group consisting of chlorine, bromine and iodine, or is a water soluble group $R^a$, $R^b$ and $R^C$ are, independently of each other, selected from the group consisting of hydrogen and optionally substituted hydrocarbyl, and n is an integer from 0 to 20.

Preferred examples of compounds of this class are:

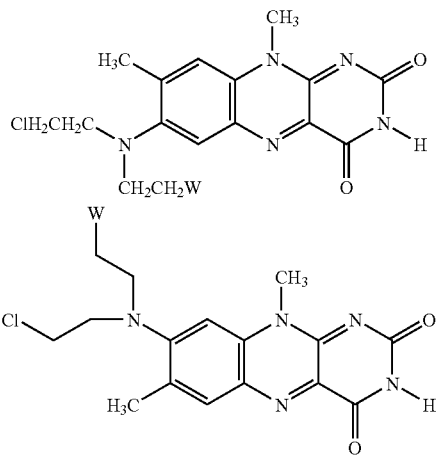

where W is a substituent imparting water solubility to the molecule, including, but not limited to, ascorbate, alcohol, polyalcohol; amine or polyamines, straight chain or cyclic saccharides, sulfates, phosphates, alkyl chains optionally substituted with —OH at any position, glycols, including polyethylene glycol and polyethers.

Another particular embodiment of compounds wherein a $R_1$, $R_2$, $R_3$, $R_4$, $R_5$ or $R_6$ that is neither H nor $CH_3$ contains a halogen or is a halogen includes compounds wherein a $R_1$, $R_2$, $R_3$, $R_4$, $R_5$ or $R_6$ that is neither H nor $CH_3$ is: X—$(CH_2)_n$—, wherein X is a halogen selected from the group consisting of chlorine, bromine and iodine, and n is an integer from 0 to 6. A preferred example of compounds of this class include:

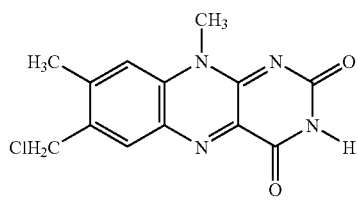

Other classes of compounds of this invention include those wherein $R_1$ is $CH_2$—$(CH_2OH)_3$—$CH_2OH$ and those wherein $R_1$ is not $CH_2$—$(CH_2OH)_3$—$CH_2OH$. Also, those compounds wherein $R_3$ and $R_6$ are H are included in the invention.

A "carbonyl compound" is any compound containing a carbonyl group (—C=O). The term "amine" refers to a primary, secondary, or tertiary amine group. A "polyamine" is a group that contains more than one amine group. A "sulfate" group is a salt of sulfuric acid. Sulfate groups include the group $(SO_4)^{2-}$. "Phosphates" contain the group $PO_4^{3-}$. "Glycols" are groups that have two alcohol groups per molecule of the compound. "Glycols" are also known as diols. A glycol is described by the formula: $C_nH_{2n}(OH)_2$, where n is an integer. An "aldehyde" is a group containing the formula —(C=O)—H. A "ketone" is a group with formula R—(C=O)—R, where R is not hydrogen. The R groups on ketone do not need to be the same. A "carboxylic acid" is a group which includes the formula: —COOH. An "ether" is a group containing —O—. A "salt" is a group where a hydrogen atom of an acid has been replaced with a metal atom or a positive radical, such as $NH_4^+$. "Ascorbate" includes groups with formula:

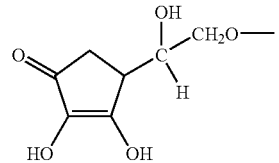

The term "hydrocarbyl" is used herein to refer generally to organic groups comprised of carbon chains to which hydrogen and optionally other elements are attached. $CH_2$ or CH groups and C atoms of the carbon chains of the hydrocarbyl may be replaced with one or more heteroatoms (i.e., non-carbon atoms). Suitable heteroatoms include but are not limited to O, S, P and N atoms. The term hydrocarbyl includes, but is not limited to alkyl, alkenyl, alkynyl, ether, polyether, thioether, straight chain or cyclic saccharides, ascorbate, aminoalkyl, hydroxylalkyl, thioalkyl, aryl and heterocyclic aryl groups, optionally substituted isoalloxazine molecules, amino acid, polyalcohol, glycol, groups which have a mixture of saturated and unsaturated bonds, carbocyclic rings and combinations of such groups. The term also includes straight-chain, branched-chain and cyclic structures or combinations thereof. Hydrocarbyl groups are optionally substituted. Hydrocarbyl substitution includes substitution at one or more carbons in the group by moieties containing heteroatoms. Suitable substituents for hydrocarbyl groups include but are not limited to halogens, including chlorine, fluorine, bromine and iodine, OH, SH, $NH_2$, COH, $CO_2H$, $OR_a$, $SR_a$, $NR_aR_b$, $CONR_aR_b$, where $R_a$ and $R_b$ independently are alkyl, unsaturated alkyl or aryl groups.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups are $C_1$–$C_6$ alkyl and include among others methyl, ethyl, n-propyl, and isopropyl groups.

The term "cycloalkyl" refers to alkyl groups having a hydrocarbon ring, particularly to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

Aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitation: vinyl, allyl, propenyl, isopropenyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, CH, $CO_2H$, $OR_c$, $SR_c$, P, PO, $NR_cR_d$, $CONR_cR_d$, and halogens, particularly chlorines and bromines where $R_c$ and $R_d$, independently, are alkyl, unsaturated alkyl or aryl groups. Preferred alkyl and unsaturated alkyl groups are the lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl ($—C_6H_5$), or naphthyl ($—C_{10}H_7$). Suitable substituents for aryl groups include among others, alkyl groups, unsaturated alkyl groups, halogens, OH, SH, $NH_2$, C.H., $CO_2H$, $OR_e$, $SR_e$, $NR_eR_f$, $CONR_eR_f$, where $R_e$ and $R_f$ independently are alkyl, unsaturated alkyl or aryl groups. Preferred substituents are OH, SH, $OR_e$, and $SR_e$ where $R_e$ is a lower alkyl, i.e., an alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as $—CO_2—$, $—CO—$, $—O—$, $—S—$, $—P—$, $—NH—$, $—CH=CH—$ and $—(CH_2)_l—$ where l is an integer from 1 to about 5, and particularly $—CH_2—$. Examples of aryl groups having bridging substituents include phenylbenzoate. Substituents also include moieties, such as $—(CH_2)_l—$, $—O—(CH_2)_l—$ or $—OCO—(CH_2)_l—$, where l is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substituents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethyl propoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethyl propoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Amino acids" as used herein include naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, o-, m-, and p-tyrosine, tryptophan, glutamine, asparagine, proline and hydroxyproline. "Amino acid" as used herein includes amino acid residues and amino acid side chains. An "amino acid residue" is an amino acid radical —NHCH(R)C(O)—, wherein R is an amino acid side chain, except for the amino acid residues of proline and hydroxyproline which are —N(CH$_2$—CH$_2$—CH$_2$)CHC(O)— and —N(CH—CHOHCH$_2$)CHC(O)—, respectively. An amino acid side chain is a radical found on the α-carbon of an α-amino acid as defined herein, where the radical is either hydrogen (side chain of glycine), methyl (side chain of alanine), or is a radical bonded to the α-carbon by a methylene (—CH$_2$—), or phenyl group.

A protected glucose derivative takes its usual meaning in the art and includes a glucose molecule wherein some of the hydroxyl groups are substituted with acetate groups.

"Straight chain or cyclic saccharides" include mono-, di- and poly-, straight chain and cyclic saccharides that are optionally substituted with an amino group which is optionally acetylated. Straight chain saccharides that are useful in this invention include but are not limited to those molecules with a chain of 5 or 6 carbon atoms with one or more —OH groups attached, and either an aldehyde or ketone group. Cyclic saccharides are saccharides that are in a ring form. Disaccharides are compounds wherein two monosaccharide groups are linked. Polysaccharides are compounds wherein more than two monosaccharide groups are linked. Specific examples of saccharides useful in this invention include glucose, ribose and glucosamine, among others.

"Isoalloxazine", "isoalloxazine derivative" or "core structure of isoalloxazine" include compounds that comprise the structure:

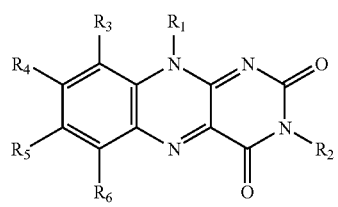

where $R_1$–$R_6$ are substituted with various substituents, as described elsewhere.

As used herein, the term "neutralization of a microorganism" or "neutralizing" means totally or partially preventing the microorganism from replicating, either by killing the microorganism or otherwise interfering with its ability to reproduce. A "neutralizer" is a compound that is capable of neutralizing a microorganism. The neutralizers useful in this invention include molecules with the core structure of isoalloxazine, as defined above. To "activate the microorganism neutralizer" is to expose the microorganism neutralizer to a triggering event that causes it to become active toward neutralizing microorganisms.

"Triggering event" refers to the stimulus that activates the microorganism neutralizer. Preferred triggering events include exposure of the neutralizer to a neutralization effective wavelength of light, or a pH sufficient to activate the neutralizer to neutralize microorganisms.

"Water soluble group" includes a group that, when included as a substituent on the neutralizer, imparts substantial solubility in water to the compound. Typically, the compound is soluble in water at a concentration of about 10–150 μM. Water soluble groups as referred to in this invention include, but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers.

"Decomposition" of the neutralizer upon exposure to light refers to the chemical transformation of the neutralizer into new compounds. An example of decomposition of the neutralizer is the production of lumichrome upon exposure of riboflavin to visible light.

An "alkylating agent" is a compound that reacts with amino acid residues and nucleic bases and inhibits replication of microorganisms.

The terms "photoactivator" and "photosensitizer" are used synonymously herein.

As used herein, "powder" means dried medium, including powder or pill. When a dried medium of a substance is described herein, it is also intended that a solution or suspension of the powder in a suitable solvent may be used, and vice versa.

The method of this invention requires mixing the photosensitizer with the material to be decontaminated. "Adding" is intended to include mixing the fluid with the photosensitizer. Mixing may be done by simply adding the photosensitizer or a solution containing the photosensitizer to a fluid to be decontaminated. In one embodiment, the material to be decontaminated to which photosensitizer has been added is flowed past a photoradiation source, and the flow of the material generally provides sufficient turbulence to distribute the photosensitizer throughout the fluid to be decontaminated. In another embodiment, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate microorganisms therein, but less than a toxic (to humans or other mammals) or insoluble amount. Excess photosensitizer may be used as long as the concentration is not so high that the photosensitizer prevents light from passing to the desired depth at a useful intensity. As taught herein, optimal concentrations for desired photosensitizers may be readily determined by those skilled in the art without undue experimentation. Preferably the photosensitizer is used in a concentration of at least about 1 micromolar. The optimum concentration of photosensitizer will vary depending on the blood component being treated and if plasma is removed, as discussed herein and in the references incorporated by reference. If red blood cells are being treated, a higher concentration of photosensitizer is desired than if plasma or platelets are being treated. If red blood cells are being treated with riboflavin, a useful concentration of riboflavin is about 1–500 micromolar, including all values and ranges therein, including 1 to 200 micromolar. A preferred concentration of riboflavin is about 300 to 500 micromolar when the plasma content is about 0 to 5% of the total volume of the solution. If plasma or platelets are being treated, a useful concentration of riboflavin is about 1–100 micromolar, and a preferred concentration of riboflavin is about 10 to 50 micromolar, including all values and ranges therein, including 10 to 30 micromolar when the plasma content is about 10–90% of the total volume of the solution.

The activated photosensitizer is capable of inactivating the microorganisms present, such as by interfering to prevent their replication. Specificity of action of the photosensitizer is conferred by the close proximity of the photosensitizer to the nucleic acid of the microorganism and this may result from binding of the photosensitizer to the nucleic acid. "Nucleic acid" includes ribonucleic acid (RNA) and deoxyribonucleic acid (DNA). Other photosensitizers may act by binding to cell membranes or by other mechanisms. The photosensitizer may also be targeted to the microorganism to be inactivated by covalently coupling to an antibody, preferably a specific monoclonal antibody to the microorganism.

The fluid containing the photosensitizer may be flowed into a photopermeable container for irradiation. The term "container" refers to a closed or open space, which may be made of rigid or flexible material, e.g., may be a bag or box or trough. It may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima™ Spectra™ and apheresis systems of GAMBRO, Inc., have been used to exemplify another embodiment involving batch-wise treatment of the fluid.

The term "photopermeable" means the material of the container is adequately transparent to photoradiation of the proper wavelength for activating the photosensitizer. In the flow-through system, the container has a depth (dimension measured in the direction of the radiation from the photoradiation source) sufficient to allow photoradiation to adequately penetrate the container to contact photosensitizer molecules at all distances from the light source and ensure inactivation of microorganisms in the fluid to be decontaminated, and a length (dimension in the direction of fluid flow) sufficient to ensure a sufficient exposure time of the fluid to the photoradiation. The materials for making such containers, depths and lengths of containers may be easily determined by those skilled in the art without undue experimentation following the teachings herein, and together with the flow rate of fluid through the container, the intensity of the photoradiation and the absorptivities of the fluid components, e.g., plasma, platelets, red blood cells, will determine the amount of time the fluid needs to be exposed to photoradiation.

In another embodiment involving batch-wise treatment, the fluid to be treated is placed in a photopermeable container which is agitated and exposed to photoradiation for a time sufficient to substantially inactivate the microorganisms. The photopermeable container is preferably a blood bag made of transparent or semitransparent plastic, and the agitating means is preferably a shaker table. The photopermeable container may be any other container, such as a rigid plastic container. The photosensitizer may be added to the container in powdered or liquid form and the container agitated to mix the photosensitizer with the fluid and to adequately expose all the fluid to the photoradiation to ensure inactivation of microorganisms.

Photosensitizer may be added to or flowed into the photopermeable container separately from the fluid being treated or may be added to the fluid prior to placing the fluid in the container. In one embodiment, photosensitizer is added to anticoagulant and the mixture of photosensitizer and anticoagulant are added to the fluid.

After treatment, the blood or blood product may be delivered to a patient, concentrated, or infused directly.

Enhancers may also be added to the fluid to make the process more efficient and selective. Such enhancers include antioxidants or other agents to prevent damage to desired fluid components or to improve the rate of inactivation of microorganisms and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, and mixtures thereof. These enhancers may be added in dried medium, including powder or pill form or in the form of liquids.

This invention also comprises fluids comprising biologically active protein, blood or blood constituents and also containing endogenous photosensitizer, endogenously-based derivative photosensitizer, or photoproduct thereof made by the inactivation methods described herein. The fluid may also contain inactivated microorganisms.

In decontamination systems of this invention, the photoradiation source may be connected to the photopermeable container for the fluid by means of a light guide such as a light channel or fiber optic tube which prevents scattering of the light between the source and the container for the fluid, and more importantly, prevents substantial heating of the fluid within the container. Direct exposure to the light source may raise temperatures as much as 10 to 15° C., especially when the amount of fluid exposed to the light is small, which can cause denaturization of blood components. Use of the light guide keeps any heating to less than about 2° C. The method may also include the use of temperature sensors and cooling mechanisms where necessary to keep the temperature below temperatures at which desired proteins in the fluid are damaged. Cooling mechanisms include flow of air or fluid, as well as other mechanisms known to the art. Preferably, the temperature is kept between about 0° C. and about 45° C., more preferably between about 22° C. and about 45° C., and preferably about 30° C., depending on the composition of the fluid. The heating of fluids from light exposure is known in the art and conditions to prevent damage to desired components of the fluids are known in the art without undue experimentation and described in the references cited herein. Usual operating temperature ranges for red blood cells are 32 to 36° C. and for platelets and plasma, below 30° C.

Any means for adding the photosensitizer to the fluid to be decontaminated and for placing the fluid in the photopermeable container known to the art may be used, such means typically including flow conduits, ports, reservoirs, sterile docking, valves, and the like. The system may include means such as pumps or adjustable valves for controlling the flow of the photosensitizer into the fluid to be decontaminated so that its concentration may be controlled at effective levels as described herein. In one embodiment, photosensitizer is mixed with the anticoagulant feed to a blood apheresis system. For endogenous photosensitizers and derivatives having sugar moieties, the pH of the solution is preferably kept low enough, as is known to the art, to prevent detachment of the sugar moiety. Preferably the photosensitizer is added to the fluid to be decontaminated in a pre-mixed aqueous solution, e.g., in water or storage buffer solution.

The photosensitizer and any optional desired additives may be placed in a container as dried medium, including powder or pill form, or as a solution. Optional additives may be chosen that help the components retain biological activity or improve the storage lifetime. These optional additives are known in the art. Desired additives and the photosensitizer may be sterilized as powders. In one embodiment, the powders desired are placed in the container prior to introduction of the fluid.

The level of plasma in the solutions may be adjusted, if desired. If the photosensitizer and any desired additives are placed in the container as one or more solutions, the volume and composition of the solution(s) may produce the desired percentage of plasma in the sample, without further additions of solution, or the percentage of plasma may be adjusted before, during or after placing said fluid in said container. Adjustment of the percentage of plasma after placing the fluid in the container may occur by the introduction of a suitable solution after the fluid is in the container. Adjustment of the percentage of plasma may occur during introduction of the fluid in a container by the introduction of a suitable solution as the fluid is being placed in the container.

The photopermeable container for the flow-through system may be a transparent cuvette made of polycarbonate, glass, quartz, polystyrene, polyvinyl chloride, polyolefin, or other transparent material. The cuvette may be enclosed in a radiation chamber having mirrored walls. A photoradiation enhancer such as a second photoradiation source or reflective surface may be placed adjacent to the cuvette to increase the amount of photoradiation contacting the fluid within the cuvette. The system preferably includes a pump for adjusting the flow rate of the fluid to desired levels to ensure substantial decontamination as described above. The cuvette has a length, coordinated with the flow rate therethrough, sufficient to expose fluid therein to sufficient photoradiation to effect substantial decontamination thereof.

Also preferably the cuvette is spaced apart from the light source a sufficient distance that heating of the fluid in the cuvette does not occur, and light is transmitted from the light source to the cuvette by means of a light guide.

In another embodiment the fluid is placed in a photopermeable container such as a blood bag, e.g. used with the apheresis system described in U.S. Pat. No. 5,653,887, and agitated while exposing to photoradiation. A photoradiation enhancer such as a second photoradiation source or reflective surface may be placed adjacent to the cuvette to increase the amount of photoradiation contacting the fluid within the cuvette. Suitable bags include collection bags as described herein. Collection bags used in the Cobe Spectra™ system or Trima™ apheresis system of GAMBRO Inc. are especially suitable. Shaker tables are known to the art, e.g. as described in U.S. Pat. No. 4,880,788. The bag is equipped with at least one port or opening for adding fluid thereto. In one embodiment the photosensitizer, preferably 7,8-dimethyl-10-ribityl-isoalloxazine, is added to the fluid-filled bag as dried medium, including powder or pill form. The bag is then placed on a shaker table and agitated under photoradiation until substantially all the fluid has been exposed to the photoradiation. Alternatively, the bag may be prepackaged with the powdered photosensitizer contained therein. The fluid to be decontaminated may then be added through the appropriate port.

Decontamination systems as described above may be designed as stand-alone units or may be easily incorporated into existing apparatuses known to the art for separating or treating blood being withdrawn from or administered to a patient. For example, such blood-handling apparatuses include the Cobe Spectra™ or GAMBRO TRIMA® apheresis systems, available from GAMBRO Inc., Lakewood, Colo., or the apparatuses described in U.S. Pat. No. 5,653,887 and U.S. Ser. No. 08/924,519 filed Sep. 5, 1997 (PCT Publication No. WO 99/11305) of GAMBRO, Inc. as well as the apheresis systems of other manufacturers. The decontamination system may be inserted just downstream of the point where blood is withdrawn from a patient or donor, just prior to insertion of blood product into a patient, or at any point before or after separation of blood constituents. The level of plasma may be adjusted, if desired, at any point before fluid is exposed to irradiation. The photosensitizer is added to blood components along with anticoagulant in a preferred embodiment, and separate irradiation sources and cuvettes are placed downstream from collection points for platelets, for plasma and for red blood cells. The use of three separate blood decontamination systems is preferred to placement of a single blood decontamination system upstream of the blood separation vessel of an apheresis system because the lower flow rates in the separate component lines allows greater ease of irradiation. In other embodiments, decontamination systems of this invention may be used to process previously collected and stored blood products.

When red blood cells are present in the fluid being treated, as will be appreciated by those skilled in the art, to compensate for absorption of light by the cells, the fluid may be thinned, exposed to higher energies of radiation for longer periods, agitated for longer periods or presented to photoradiation in shallower containers or conduits than necessary for use with other blood components.

The endogenous photosensitizers and endogenously-based derivative photosensitizers disclosed herein can be used in pre-existing blood component decontamination systems as well as in the decontamination system disclosed herein. For example, the endogenous photosensitizers and endogenously-based derivative photosensitizers of this invention can be used in the decontamination systems described in U.S. Pat. Nos. 5,290,221, 5,536,238, 5,290,221 and 5,536,238.

A photoradiation enhancer, such as a reflective surface may also be provided in any method or apparatus of the invention. The light may be guided to impinge on the fluid in any desired manner, including positioning the fluid in the light path of the light source, using a light guide, or other methods. The apparatuses of the invention may also comprise components such as a temperature monitor, temperature controller, means for flowing said fluid into and out of said container, means for agitating said fluid in said container, and other desired components to control various aspects of the system. The temperature controller may be a fan directed toward the light source, directed on the fluid, or both. One or more temperature controllers may be used to cool different components to different levels.

The methods of the invention may be used in a kit, for example, a kit to determine if a virus or parasite (or other microorganism) is present in blood or a blood component.

For example, one kit includes a sample of blood or a blood component that has been inactivated by the methods of the invention. This inactivated sample is compared to a non-inactivated sample to determine if a virus or parasite (or other microorganism) is present in the blood or a blood component or other sample.

BRIEF DESCRIPTION OF THE DRAWINGS

FIG. 5 shows the log reduction in West Nile virus in plasma using various amounts of energy applied.

DETAILED DESCRIPTION OF THE INVENTION

Figure 1:
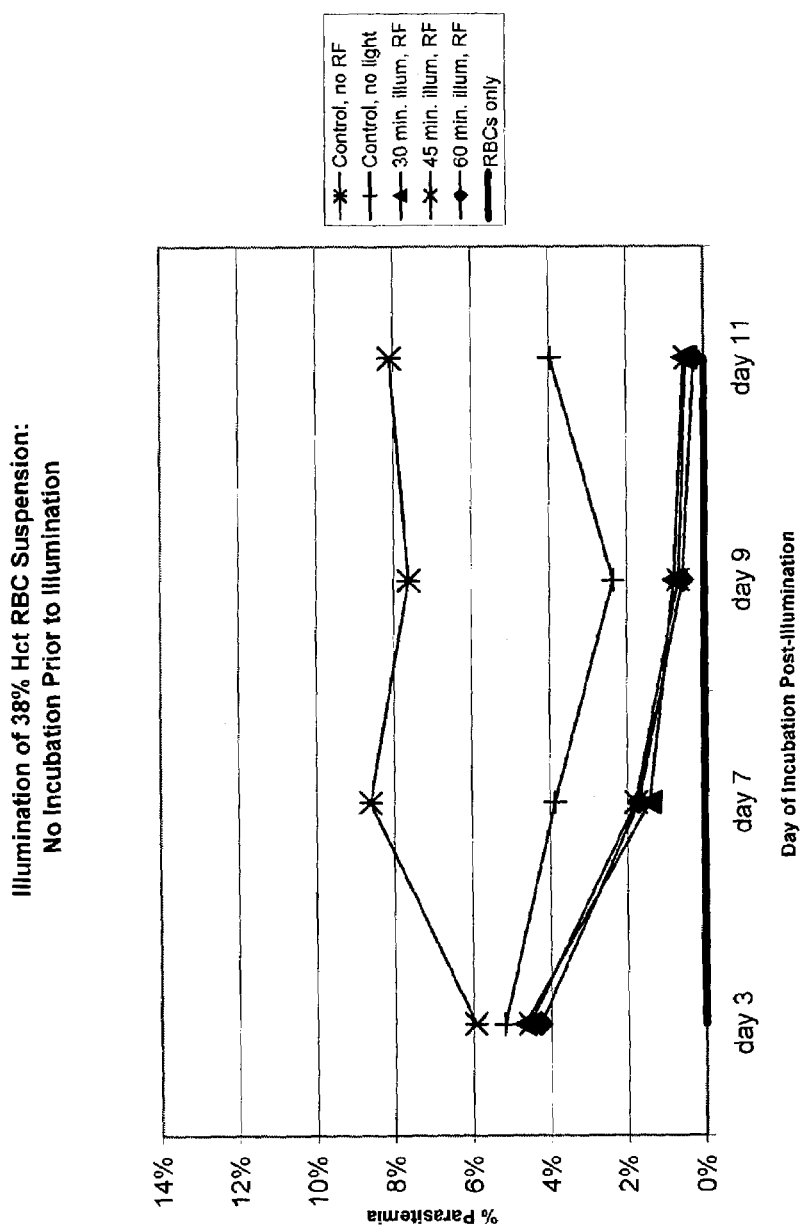
FIG. 1 shows *P. falciparum* inactivation results from 38% Hct red blood cell samples with no incubation prior to illumination.

The following applications are hereby incorporated by reference to the extent not inconsistent with the disclosure herewith: U.S. patent application Ser. No. 10/104,766, filed Mar. 21, 2002; U.S. patent application Ser. No. 10/247,262 filed Sep. 18, 2002; U.S. provisional application Ser. No. 60/368,778, filed Mar. 28, 2002; U.S. patent application Ser. No. 10/159,781, filed May 30, 2002; U.S. patent application Ser. No. 09/982,298, filed Oct. 16, 2001; U.S. patent application Ser. No. 10/328,717, filed Dec. 23, 2002; U.S. patent application Ser. No. 10/065,073, filed Sep. 13, 2002; U.S. patent application Ser. No. 09/962,029, filed Sep. 25, 2001; U.S. provisional application Ser. No. 60/353,223, filed Feb. 1, 2002; U.S. provisional application Ser. No. 60/355,393, filed Feb. 8, 2002; U.S. provisional application Ser. No. 60/377,697, filed May 3, 2002; U.S. patent application Ser. No. 10/325,402, filed Dec. 20, 2002; U.S. provisional application Ser. No. 60/353,319, filed Feb. 1, 2002; U.S. provisional application Ser. No. 60/379,328, filed May 8, 2002; U.S. provisional application Ser. No. 60/375,734, filed Apr. 26, 2002; U.S. provisional application Ser. No. 60/373,198, filed Apr. 16, 2002; U.S. provisional application Ser. No. 60/373,936, filed Apr. 19, 2002; U.S. provisional application Ser. No. 60/378,374, filed May 6, 2002; U.S. provisional application Ser. No. 60/375,849, filed Apr. 24, 2002; U.S. patent application Ser. No. 09/586,147, filed Jun. 2, 2000; U.S. patent application Ser. No. 09/596,429, filed Jun. 15, 2000; U.S. provisional application Ser. No. 60/375,670, filed Apr. 26, 2002; PCT patent application Ser. No. PCT/US02/21925, filed Jul. 12, 2002; U.S. provisional application Ser. No. 60/319,488, filed Aug. 23, 2002; U.S. provisional application Ser. No. 60/319,641, filed Oct. 22, 2002; U.S. patent application Ser. No. 09/119,666, filed Jul. 21, 1998 (U.S. Pat. No. 6,258,577); U.S. patent application Ser. No. 09/357,188, filed Jul. 20, 1999 (U.S. Pat. No. 6,277,337); U.S. patent application Ser. No. 09/420,652, filed Oct. 19, 1999 (U.S. Pat. No. 6,268,120); U.S. patent application Ser. No. 09/777,727, filed Feb. 5, 2001; U.S. patent application Ser. No. 10/256,852, filed Sep. 26, 2002; U.S. patent application Ser. No. 09/725,426, filed Nov. 28, 2000. The present invention includes all aspects of the cited applications and patents that are not inconsistent with the disclosure herewith. For example, apparatuses and systems other than those specifically exemplified in the disclosure herewith are included in the cited applications and patents and are included herein.

The decontamination method of this invention using endogenous photosensitizers and endogenously-based derivative photosensitizers is exemplified herein using 7,8-dimethyl-10-ribityl isoalloxazine as the photosensitizer, however, any photosensitizer may be used which is capable of being activated by photoradiation to cause inactivation of microorganisms. The photosensitizer must be one which does not substantially destroy desired components of the fluid being decontaminated, and also preferably which does not break down as a result of the photoradiation into products which significantly destroy desired components or have significant toxicity. The wavelength at which the photosensitizer is activated is determined as described herein, using literature sources or direct measurement. Its solubility in the fluid to be decontaminated or in a combination of carrier fluid and fluid to be contaminated is also so determined. The ability of photoradiation at the activating wavelength to penetrate the fluid to be decontaminated is also determined as taught herein and known in the art. Appropriate temperatures for the reaction of the photosensitizer with its substrate are determined, as well as the ranges of temperature, photoradiation intensity and duration and photosensitizer concentration which will optimize microbial inactivation and minimize damage to desired proteins and/or cellular components in the fluid.

Once such system requirements have been determined for flow-through systems, apparatuses may be designed which provide the correct flow rates, photopermeabilities, plasma contents, light wavelengths and light intensities to cause inactivation of microorganisms present in the fluid, as is taught herein. In one embodiment, the fluid is mixed with photosensitizer and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, which may be increased through the use of light guides to carry the photoradiation directly to the container for the fluid, an appropriate photopermeable material for the container for the fluid, an appropriate depth to allow full penetration of the photoradiation into the container, photoradiation enhancers such as one or more additional photoradiation sources, preferably on the opposite side of the container from the first, or reflectors to reflect light from the radiation source back into the container, appropriate flow rates for the fluid in the container and an appropriate container length to allow sufficient time for inactivation of microorganisms present. Temperature monitors and controllers may also be required to keep the fluid at optimal temperature.

For batch systems, it is preferred to place the fluid to be decontaminated along with photosensitizer in bags which are photopermeable or at least sufficiently photopermeable to allow sufficient radiation to reach their contents to activate the photosensitizer. Sufficient photosensitizer is added to each bag to provide inactivation, and the bag is preferably agitated while irradiating, for a period of time to ensure exposure of substantially all the fluid to radiation. The photosensitizer may be added in powdered form.

The method preferably uses endogenous photosensitizers, including endogenous photosensitizers which function by interfering with nucleic acid replication. 7,8-dimethyl-10-ribityl isoalloxazine is the preferred photosensitizer for use in this invention. The chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). Cadet et al. (1983) J. Chem., 23:420–429, clearly demonstrate the effects of 7,8-dimethyl-10-ribityl isoalloxazine are due to non-singlet oxygen oxidation of guanosine residues. In addition, adenosine bases appear to be sensitive to the effects of 7,8-dimethyl-10-ribityl isoalloxazine plus UV light. This is important since adenosine residues are relatively insensitive to singlet oxygen-dependent processes. 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species. Since indiscriminate damage to cells and proteins arises primarily from singlet oxygen sources, this mechanistic pathway for the action of 7,8-dimethyl-10-ribityl isoalloxazine allows greater selectivity in its action than is the case with compounds such as psoralens which possess significant Type II chemistry.

7,8-dimethyl-10-ribityl isoalloxazine (Riboflavine or vitamin B2) absorbs light from about 200 to 500 nm. The ring system core of 7,8-dimethyl-10-ribityl isoalloxazine is resistant to photodegradation but the ribityl side chain of riboflavin undergoes photodegradation. Photolysis of 7,8-dimethyl-10-ribityl isoalloxazine may form lumichrome (7,8-dimethylalloxazine) depending on conditions. 7,8-dimethylalloxazine strongly absorbs ultraviolet (UV) light and only weakly absorbs visible light.

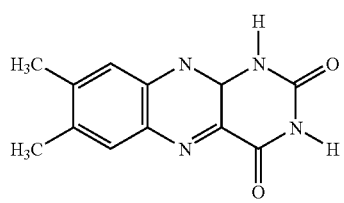

7,8-dimethylalloxazine

As a result of the degradation of 7,8-dimethyl-10-ribityl isoalloxazine upon exposure to light, a combination of visible and ultraviolet light is preferred in decontamination procedures using 7,8-dimethyl-10-ribityl isoalloxazine. Since UV light has a higher energy per photon than visible light, and because UV light is absorbed more strongly than visible light by useful compounds in the biological fluid, more damage to the useful components in the biological fluid containing the contaminants will occur when ultraviolet light is used in combination with visible light than when visible light can be used alone.

The methods of this invention do not require the use of enhancers such as "quenchers" or oxygen scavengers, however these may be used to enhance the process by reducing the extent of non-specific cell or protein-damaging chemistry or enhancing the rate of pathogen inactivation. Further preferred methods using non-toxic endogenous photosensitizers and endogenously-based derivative photosensitizers do not require removal of photosensitizers from the fluid after photoradiation.

Apparatus Design

The methods of the invention may be used in a variety of devices. The devices generally comprise: a light source producing light having sufficient wavelength and power to induce inactivation of microorganisms which may be present in a sample; and means for positioning the sample so that it receives energy of sufficient wavelength and power to induce inactivation of microorganisms.

The system preferably includes means for producing movement in the sample. Movement provides many benefits including improving the efficiency of the inactivation reactions by helping mix the photosensitizer with the fluid to be deactivated and providing turnover of sample at the container-light interface, for example. An agitator, such as a Helmer flatbed agitation system (Helmer) may be used. This agitator provides oscillatory motion. Other types of agitators may be used to provide motion normal to the bag. If a bag is used as a container, in combination with a source of movement, a pin or other structure may be placed across or within the bag to provide turbulent eddies in the fluid. The agitator may be connected to a computer or other controller in an inactivation system. Some parameters that may be controlled or monitored include temperature of the fluid, energy output of the lights, agitation motion, light control, timing control or monitoring, and other parameters. The light source and fluid being treated may both move to provide agitation of the fluid, or only the fluid being treated may move while the light source remains stationary.

One particular embodiment of the apparatus is an enclosed photoradiation system where the sample would be placed in an apparatus similar to the Bio-Genic irradiator (Vilber-Lourmat, Cedex, France) that uses the appropriate wavelength or wavelengths. Another embodiment is a conveying apparatus used in a large-scale operation to carry samples through a light field or series of light fields.

Means for positioning the sample so that it receives energy of sufficient wavelength and power to induce inactivation of microorganisms include a shelf or tray for the sample to be disposed upon; a gap between two supports which may be a light or light arrays, where the sample is positioned between the supports; or other means as known in the art. The shelf or tray may move, as in a conveyer line. Fluid-holding shelves may be transparent to one or more of the wavelength(s) of light applied.

The sample may be placed in a suitable container on a support surface between two or more sources of photoradiation, like a sandwich. Alternatively, one of the photoradiation-sources may be a reflective material, to allow the light to contact both sides of the sample. Alternatively, or in combination, the sample may be placed on a support and light may impinge on one surface, with agitation, to allow different portions of the sample to be in contact with the light.

Different sources of photoradiation may be used, depending on the wavelength desired and the power desired at the desired wavelength. One light source that may be used has an emission centered around 447 nm.

Lights that emit in the blue spectral range come from various sources. Lamps with peak emissions around 420 to 450 nm may be purchased from LCD Lighting, Orange, Conn.; Bulbtronic, Farmingdale, N.Y.; National Biological Corp., Twinsburg, Ohio; The Fluorescent Co., Saugus, Calif.; Tek-West, Los Angeles, Calif.; or Southern NE UV, Bransford, Conn., for example. LED (light emitting diodes) may also be used. These LEDs may use a variety of materials to produce the desired spectral output, including silicon carbide (bandwidth around 100 nm; peak spectral output near 466 nm) or gallium nitride (bandwidth around 30–35 nm; peak spectral output near 470 nm). Also, lights made from a combination of different materials can generate different wavelengths of light. For example, gallium nitride on a silicon carbide substrate can generate 430 nm. These LEDs are manufactured or distributed by Panasonic, Chicago Miniature, Nichia, Toyoda Gosei, Hewlett Packard, LEDTronics, for example. LED lights typically do not require any outside cooling.

The lights may be used in different ways, depending the particular apparatus. For example, diodes may be duty cycled to emit light when the sample arrives in a flow cell light path. Arrays of diodes may surround the fluid in any desired configuration. In a flat bed apparatus, light arrays may surround the fluid from top or bottom, or both.

Filters, such as color glass filters, may be used to isolate a desired band of the spectrum. Single wavelength or narrow band sources may also be used.

One embodiment of an apparatus useful in the methods of the invention includes banks of interchangeable lights that produce the desired wavelength of light for the particular fluid being treated. A coral or aquarium light may be used to produce wavelengths between 440 and 470 nm that is useful in inactivating microorganisms in red blood cells. The lamps may be provided with separate power supplies to control the level of light output. These lamps may be sequentially placed in position to impinge light on the sample, or the sample may travel through lights of different wavelengths. Different LEDs emitting each desired wavelength may be combined in one array.

Active (cooling through some applied means) or passive (air cooling) cooling may be used if necessary to cool either the lamps or the blood. Fans may provide cooling. One set of fans may be used to cool both the lamps and blood, or different fans may be used to provide different levels of cooling to both the lamps and the blood. A photopermeable fluid may surround the sample and/or lights to provide active cooling. This fluid may be optionally temperature controlled.

Malaria Inactivation

Inactivation of the malaria parasite *Plasmodium falciparum* in red blood cells was tested using Riboflavin (RF) and visible light. Inactivation of the malaria parasite *Plasmodium falciparum* in other blood components and with other regions of light proceeds analogously, and is well within the skill of one of ordinary skill in the art using the teachings herein and in the references incorporated by reference. Effectiveness of the method was evaluated with measurements of parasite viability in treated units compared to that in controls. Infected red cells were treated at two different hematocrits: 6%, with 4% of the red cells infected, and 38%, with 0.4% of the red cells infected. In each test, the parasite viability decreased to background levels during post-treatment incubation, indicating that riboflavin and light inactivate *P. falciparum*.

Parasite Inoculum:

*Plasmodium falciparum* parasite (strain NF54 [Ponnudurai T, et al. The production of mature gametocytes of *Plasmodium falciparum* in continuous culture of different isolates infective to mosquitoes. *Trans Roy Soc Trop Med Hyg*. 1982;76:242]) was cultivated from a continuous stock culture (modified Trager and Jensen technique [Trager W, Jensen J B. Human malaria parasites in continuous culture. *Science*. 1976; 193:673]) maintained at the Walter Reed Army Institute of Research Malaria Culture Laboratory. The inoculum was prepared with 5 mL of stock culture, 95 mL of RPMI media, and 6% human red blood cells (RBCs) and incubated at 37° C. and 100 rpm after brief exposure to 5% $CO_2$, 5% $O_2$, and 90% $N_2$ gas. The inoculum media was changed daily when the parasitemia was below 5%, and twice daily for parasitemia greater than 5%.

Donor Red Blood Cells

Blood from volunteer donors was collected into citrate-phosphate-dextrose (CPD). The donor whole blood units were centrifuged at 5,000 g for 10 minutes; after centrifugation, plasma and some of the buffy-coat was removed and discarded, leaving packed RBCs (pRBCs).

Preparation for Illumination

The parasite inoculum was centrifuged and the supernatant was removed. For Illumination of Inoculum only:

16 mL of parasite inoculum and 24 mL of 500 µM riboflavin solution added to 150-mL PVC bag with 10 mL of air for a Hct=6% and parasitemia=4%

Incubation for 1 hour at room temperature with mixing prior to illumination

For Illumination of Red Cells at 38% Hct:

10 mL of pRBCs combined with 6 mL parasitized inoculum and 500 µM riboflavin solution to volume of 40 mL with Hct=38% and parasitemia=0.4%

One set of tests at 38% Hct involved illumination directly after preparation of the suspension (No Incubation); the other set of tests at 38% Hct involved incubation for 1-hr at room temperature with mixing prior to illumination (With Incubation).

Samples of 0.3 mL were removed from all suspensions before illumination.

Illumination

After preparation, and incubation with the riboflavin solution, red cell suspensions were illuminated with 450 nm light for 30, 45, or 60 minutes in 150 mL DEHP bags, CharterMed.

Energy delivered was 60, 90, and 120 $J/cm^2$, respectively.

After illumination, 1-mL samples were removed from each suspension.

Sample Preparation and Analysis

Parasite viability was examined by measuring parasitic lactate dehydrogenase (pLDH) levels with a double monoclonal antibody ELISA technique (Druilhe, P., et al. A calorimetric in vitro drug-sensitivity assay for *P. falciparum* based on a highly sensitive two-site LDH antigen capture ELISA assay. *Am J Trop Med Hyg* 2001 May–June; 64:233–41). Measurements of pLDH correlate linearly with % parasitemia. Viability of the parasite is reflected in pLDH. Samples removed prior to illumination were prepared for the assay and stored immediately. Samples removed after illumination were incubated for 2 weeks in multi-well plates with RPMI and aliquots were periodically removed, prepared for the assay, and stored. At the end of the 2-week incubation, all samples were assayed for pLDH content. % Parasitemia of the parasitic inoculum was determined from counts of infected RBCs per total number of RBCs; this value and the pLDH values for untreated inoculum and uninoculated RBCs were used to determine a proportionality constant relating pLDH to % parasitemia:

$\kappa$=% Parasitemia of Inoculum/($pLDH_{inoculum}$−$pLDH_{uninoculatedRBCs}$)

The proportionality constant, κ, is used to calculate % Parasitemia for all samples:

$$\% \text{ Parasitemia of Sample} = \kappa^*(\text{pLDH}_{sample} - \text{pLDH}_{uninoculatedRBCs})$$

Results

Figure 2:
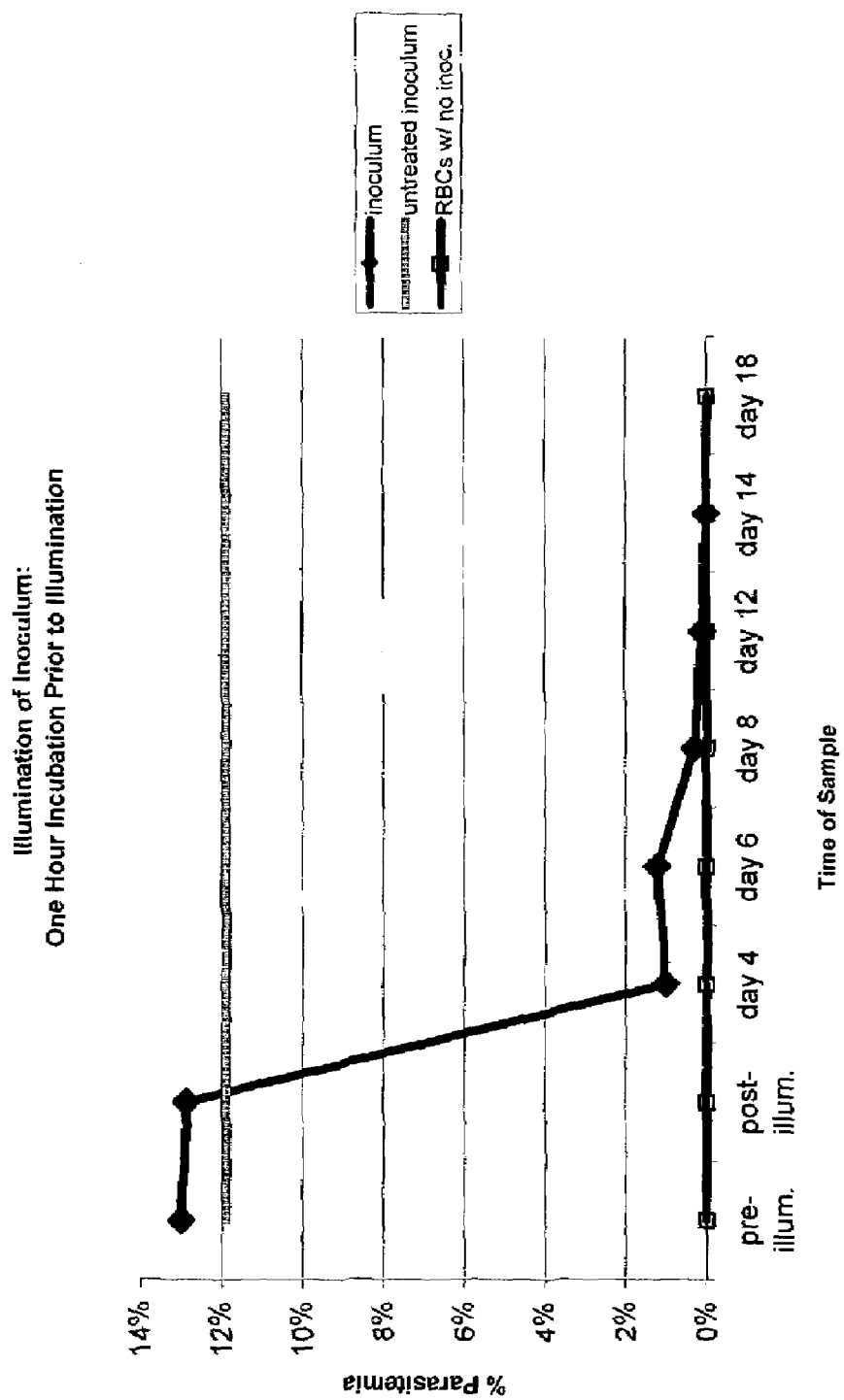
FIG. 2 shows *P. falciparum* inactivation results from illuminating the innoculum (no red blood cells).
Figure 3:
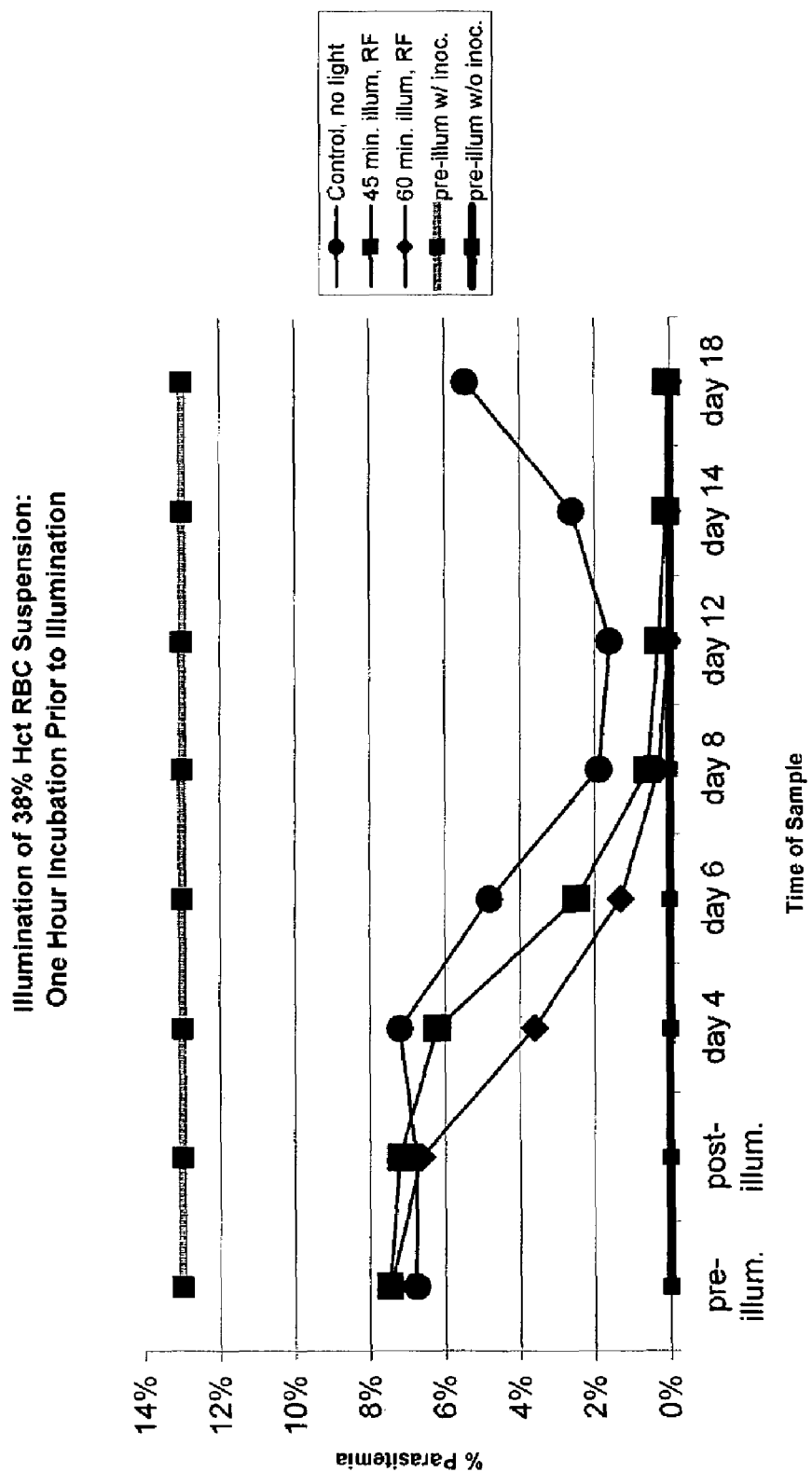
FIG. 3 shows *P. falciparum* inactivation results from illuminating 38% Hct red blood cell suspension that was incubated for 1 hour prior to illumination.

FIG. 1 shows inactivation results from 38% Hct RBC samples with no incubation prior to illumination. FIG. 2 shows inactivation results from illuminating the innoculum (no RBCs). FIG. 3 shows inactivation results from illuminating 38% Hct RBC suspension that was incubated for 1 hour prior to illumination.

The results indicate that riboflavin and visible light significantly reduce parasite viability. Treatment of low Hct inoculum yielded most rapid reduction in parasite viability. Illumination of red cell suspension after 1 hour of incubation with riboflavin solution yielded more rapid reduction in parasite viability than illumination without incubation. Unilluminated controls with riboflavin solution exhibited decreased parasite viability over short incubation times; over longer times, parasite viability recovered.

West Nile Virus (WNV) Inactivation

Inactivation of the West Nile virus (New York 1999, flamingo, 35262-11, from CDC Laboratories, Fort Collins, Colo.) was tested using riboflavin (RF) and visible light for RBCs and riboflavin (RF) and ultraviolet light for plasma and platelets. Titers were determined using the Tissue Culture Infectious Dose (TCID50) method (the dose where 50% of the wells are infected) with Vero cells (African green monkey kidney cells). This is a standard technique known to those skilled in the art and is described in the following references: Karber, G. 1931 Beitrag zur kollektiven Behandlung pharmakologisher Reihenversuche. Arch. Exp. Pathol. Pharmakol. 162: 480–483; Reed, L. J., and H. Meunch. 1938. A sample method for estimating fifty percent endpoints. Am. J. Hyg. 27:493–497; Leland, D. S., and M. L. V. French. 1988. Virus Isolation and Identification, p. 39–59, In A. Balows, W. J. Hausler, and E. H. Lennette (eds.), Laboratory Diagnosis of Infectious Diseases, Principles and Practice. Volume II: Viral, Rickettsial, and Chlamydial Diseases. Springer-Verlag, New York. The Vero cells were fed with DMEM supplemented with 10% fetal bovine serum (Hyclone). The amount of virus that was added to each component was a certain number of plaque-forming units (pfu) based on a titration of the virus in a plaque assay test (infected cells covered by a nutrient agar overlay). The endpoint for testing was based on cytopathic effect (CPE) where the tissue cultured in wells is looked at with a microscope to determine if the virus has infected the cells to determine the 50% tissue culture infectious dose. The samples were incubated at 37° C., 5% $CO_2$ for 5 days and monitored daily. A 50 μL inoculum size was used. The results for sample size n=3 for each blood component are reported. Each run used RBCs, plasma or platelets from a different donor.

Platelet Study

Figure 4:
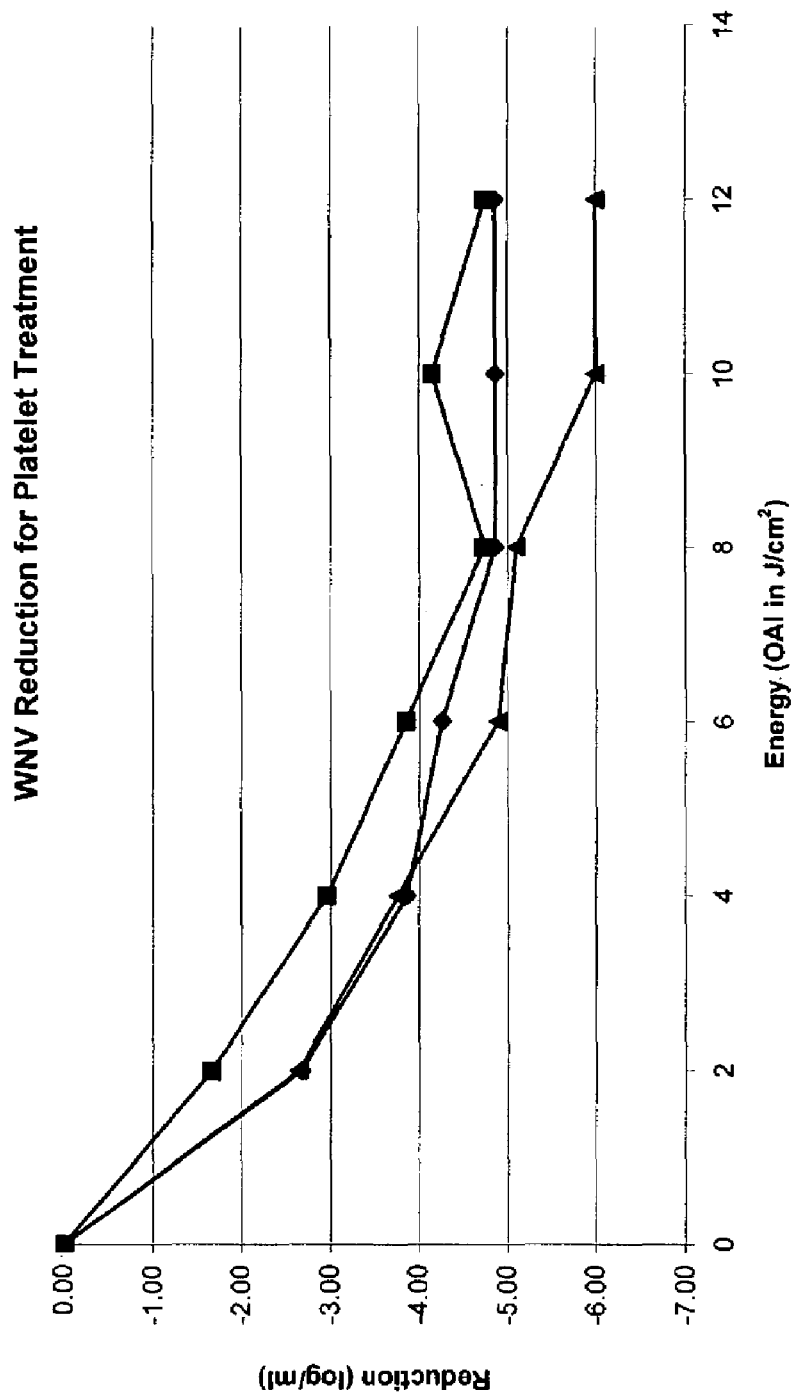
FIG. 4 shows the log reduction in West Nile virus in platelets using various amounts of energy applied.

A volume of 250 mL of platelets was used with 50 μM riboflavin. The platelets were illuminated with light having a peak at 320 nm to deliver 2, 4, 6, 8, 10 or 12 j/cm². FIG. 4 shows the log reduction in WNV using various amounts of energy applied.

Figure 5:
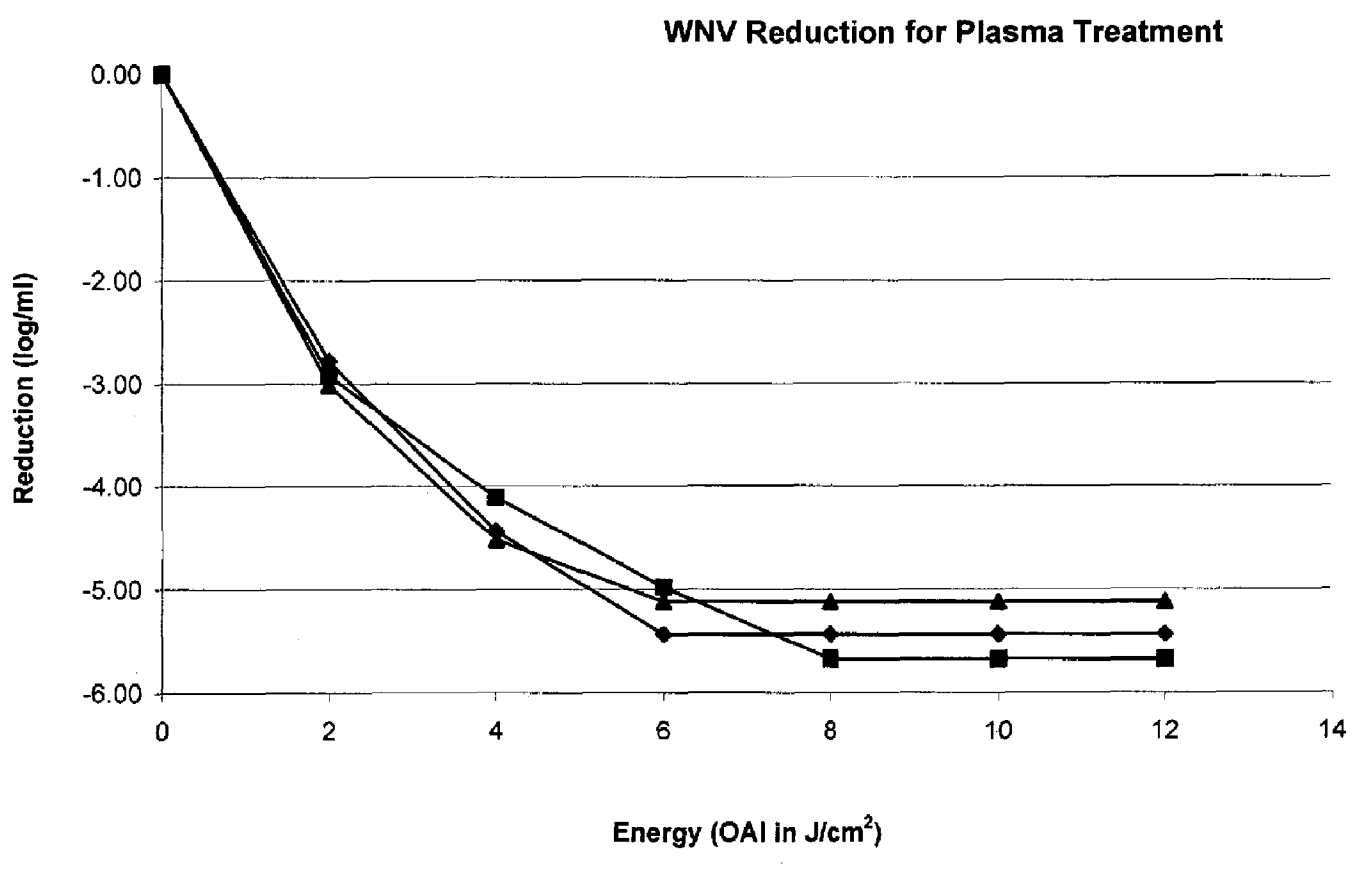

Plasma Study 250 mL plasma was used with 50 μM riboflavin. The plasma was illuminated with lights having a peak wavelength at 320 nm to deliver 2, 4, 6, 8, 10 or 12 J/cm². FIG. 5 shows the log reduction in WNV using various amounts of energy applied.

Red Blood Cell Study

Figure 6:
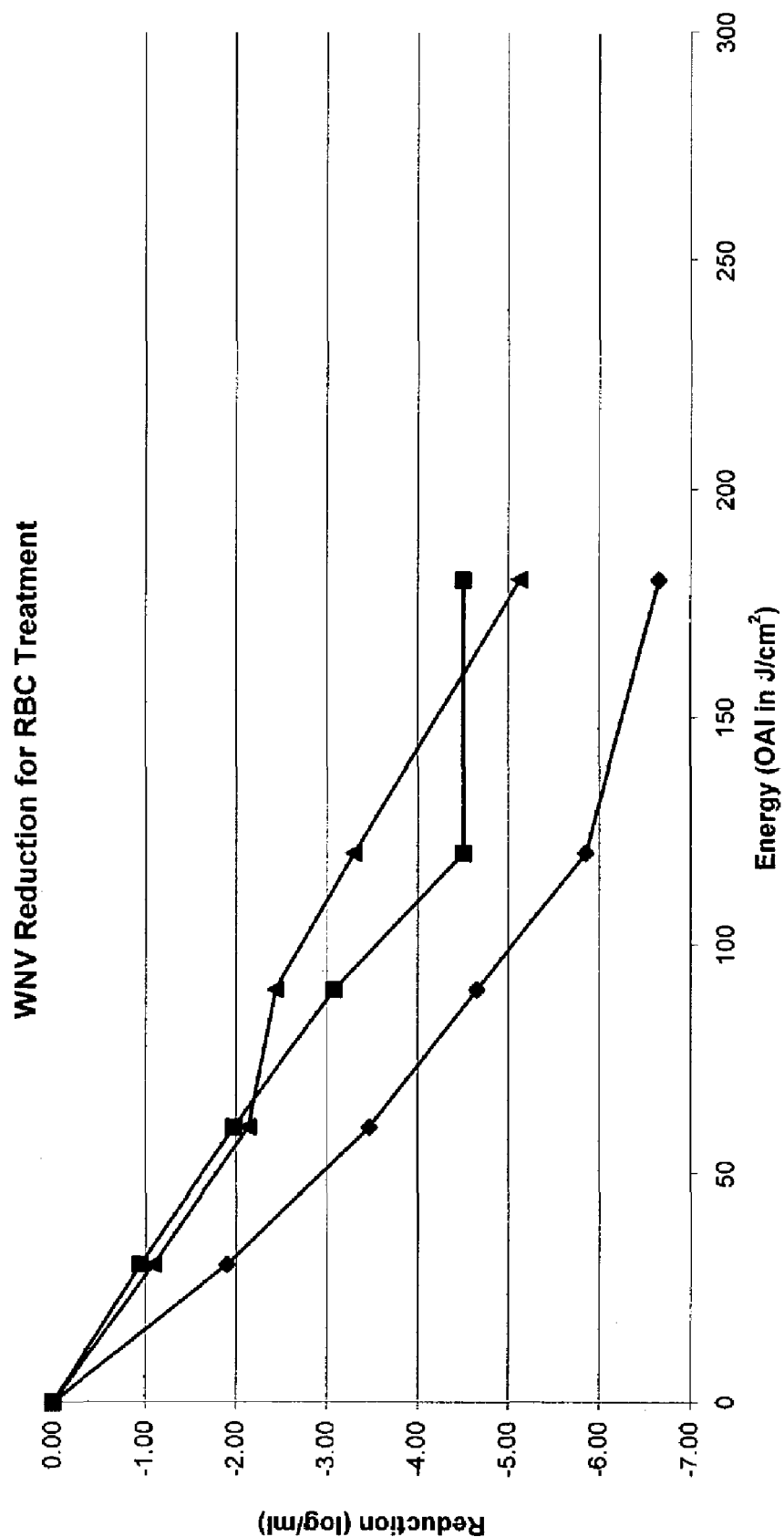
FIG. 6 shows log reduction in West Nile virus in red blood cells using various amounts of energy applied.

The product volume was 266 mL at 30 Hct. The riboflavin concentration was about 500 μM. Visible light (400 to 520 nm) was used. The RBCs were illuminated to deliver was 30, 60, 90, 120 or 180 J/cm². FIG. 6 shows log reduction in WNV using various amount of energy applied.

Results

The result show a reduction in the viral titers of platelets, plasma and red blood calls infected with West Nile Virus.

TABLE 1

| Energy Delivered, J/cm² | Reduction of WNV in RBCs, log/mL | | |
|---|---|---|---|
| 0 | 0.00 | 0.00 | 0.00 |
| 30 | 1.90 | 0.95 | 1.09 |
| 60 | 3.47 | 1.98 | 2.14 |
| 90 | 4.65 | 3.07 | 2.44 |
| 120 | 5.85 | ≧4.50 | 3.30 |
| 180 | ≧6.65 | ≧4.50 | ≧5.13 |

TABLE 2

| Energy Delivered, J/cm² | Reduction of WNV in Platelets, log/mL | | |
|---|---|---|---|
| 0 | 0.00 | 0.00 | 0.00 |
| 2 | 2.67 | 1.66 | 2.64 |
| 4 | 3.86 | 2.96 | 3.76 |
| 6 | 4.26 | 3.85 | 4.89 |
| 8 | ≧4.86 | ≧4.50 | 5.10 |
| 10 | ≧4.86 | ≧4.15 | ≧6.00 |
| 12 | ≧4.86 | ≧4.75 | ≧6.00 |

TABLE 3

| Energy Delivered, J/cm² | Reduction of WNV in Plasma, log/mL | | |
|---|---|---|---|
| 0 | 0.00 | 0.00 | 0.00 |
| 2 | 2.78 | 2.92 | 3.01 |
| 4 | 4.44 | 4.11 | 4.52 |
| 6 | ≧5.44 | 4.98 | ≧5.12 |
| 8 | ≧5.44 | ≧5.68 | ≧5.12 |
| 10 | ≧5.44 | ≧5.68 | ≧5.12 |
| 12 | ≧5.44 | ≧5.68 | ≧5.12 |

We claim:

1. A method for treating a fluid to inactivate at least one type of parasite or virus that may be present therein, said fluid containing one or more components selected from the group consisting of: biologically active protein, blood, and blood constituents, without destroying the biological activity of such component, comprising:
   (a) adding an inactivation effective, substantially non-toxic amount of an endogenous photosensitizer or endogenously-based derivative photosensitizer other than a porphyrin to the fluid; and
   (b) exposing the fluid of step (a) to photoradiation sufficient to activate the photosensitizer, whereby at least one parasite or virus in the fluid is inactivated.

2. The method of claim 1, wherein the parasite comprises *P. falciparum*.

3. The method of claim 1, wherein the fluid comprises red blood cells and the photoradiation has a wavelength of about 447 nm.

4. The method of claim 1, further comprising adding air to the fluid and photosensitizer before exposing the fluid to photoradiation.

5. The method of claim 1, wherein the photosensitizer is a nucleic-acid-targeted non-toxic, photoactivatable compound which does not produce toxic photolytic breakdown products.

6. The method of claim 1, wherein the photosensitizer is endogenous.

7. The method of claim 6, wherein the photosensitizer is 7,8-dimethyl-10-ribityl isoalloxazine.

8. The method of claim 1, wherein the virus comprises West Nile virus.

9. The method of claim 1, wherein the photoradiation comprises one or more wavelengths in the visible spectrum.

10. The method of claim 1, wherein the photoradiation comprises one or more wavelengths in the ultraviolet spectrum.

11. The method of claim 1, wherein said fluid of step (a) is exposed to a source of photoradiation at a depth selected to ensure penetration of the photoradiation through the fluid and inactivation of the parasite or virus.

12. The method of claim 1, wherein the fluid comprises blood constituents.

13. The method of claim 1, wherein the fluid is whole blood.

14. The method of claim 1, wherein the fluid is a separated blood product.

15. The method of claim 1, wherein an endogenous photosensitizer is added to anticoagulant and said anticoagulant is added to the fluid.

16. The method of claim 1, wherein the photosensitizer is capable of inactivating viruses or parasites at a pH of about 7.4.

17. The method of claim 1, wherein the photosensitizer is capable of inactivating viruses or parasites in the presence of plasma, cells or blood components.

18. The method of claim 1, wherein the photosensitizer inactivates at least one type of parasite or virus present in human blood.

* * * * *